United States Patent [19]

Serban et al.

[11] 4,409,017
[45] Oct. 11, 1983

[54] HERBICIDAL ISOQUINOLINOXY- OR ISOQUINOLINAMINO-PHENOXY ALKANE CARBOXYLIC ACID DERIVATIVES

[75] Inventors: Alexander Serban, Doncaster; Graham J. Bird, North Melbourne; Lindsay E. Cross, Maribyrnong, all of Australia

[73] Assignee: ICI Australia Limited, Melbourne, Australia

[21] Appl. No.: 274,164

[22] Filed: Jun. 16, 1981

[30] Foreign Application Priority Data

Jul. 1, 1980 [AU] Australia ............................ PE4317
Dec. 22, 1980 [AU] Australia ............................ PE7035

[51] Int. Cl.$^3$ ............... A01N 43/42; C07D 217/22; C07D 217/24
[52] U.S. Cl. ........................ 71/94; 546/141; 546/142; 546/143
[58] Field of Search ............ 546/141, 142, 143; 71/94

[56] References Cited

U.S. PATENT DOCUMENTS

| | | | |
|---|---|---|---|
| 3,930,837 | 1/1976 | Serban | 71/94 |
| 4,236,912 | 12/1980 | Johnston et al. | 71/94 |
| 4,259,105 | 3/1981 | Maeda et al. | 71/108 |
| 4,310,347 | 1/1982 | Serban et al. | 71/93 |
| 4,314,065 | 2/1982 | Serban et al. | 548/222 |

FOREIGN PATENT DOCUMENTS

| | | | |
|---|---|---|---|
| 881815 | 8/1980 | Belgium. | |
| 52-72821 | 6/1977 | Japan | 71/94 |
| 55-143970 | 11/1980 | Japan | 71/94 |
| 2042539 | 9/1980 | United Kingdom | 71/94 |

*Primary Examiner*—Diana G. Rivers
*Attorney, Agent, or Firm*—Cushman, Darby & Cushman

[57] ABSTRACT

The invention concerns novel compounds of the formula I

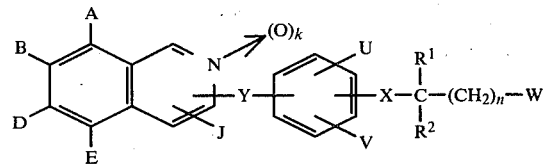

The compounds are herbicides and in further embodiments the invention provides: processes for the preparation of compounds of formula I; intermediates useful in the preparation of compounds of formula I; compositions containing as active ingredient compounds of formula I; and processes for severely damaging or killing unwanted plants by applying to the plants or to the growth medium of the plants an effective amount of a compound of formula I.

8 Claims, No Drawings

HERBICIDAL ISOQUINOLINOXY- OR ISOQUINOLINAMINO-PHENOXY ALKANE CARBOXYLIC ACID DERIVATIVES

This invention relates to organic compounds having biological activity and in particular to organic compounds having herbicidal properties, to processes for the preparation of such compounds, to intermediates useful in the preparation of such compounds and to herbicidal compositions and processes utilizing such compounds.

We have now found a new class of isoquinolines which exhibit biological activity, and in particular herbicidal activity.

Accordingly the invention proves a compound of formula I:

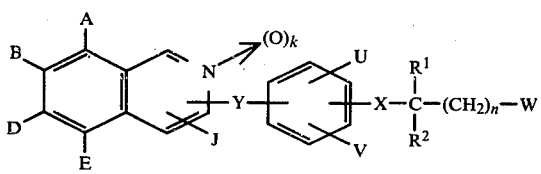

or a salt thereof wherein:

A, B, D, E, J, U and V are independently chosen from the group consisting of hydrogen, halogen, nitro, cyano, thiocyano, amino, $C_1$ to $C_6$ alkylamino, di($C_1$ to $C_6$ alkyl)amino, $C_1$ to $C_6$ alkyl, $C_1$ to $C_6$ haloalkyl, $C_2$ to $C_6$ alkenyl, $C_3$ to $C_7$ cycloalkyl, $C_1$ to $C_6$ alkoxy, $C_1$ to $C_6$ haloalkoxy, $C_1$ to $C_6$ alkylthio, $C_1$ to $C_6$ alkylsulfinyl, $C_1$ to $C_6$ alkylsulfonyl, $C_1$ to $C_6$ haloalkylsulfinyl, $C_1$ to $C_6$ haloalkylsulfonyl, sulfo, $C_1$ to $C_6$ alkoxysulfonyl, sulfamoyl, N-($C_1$ to $C_6$ alkyl)sulfamoyl, N,N-di($C_1$ to $C_6$ alkyl)sulfamoyl, carboxy, ($C_1$ and $C_6$ alkoxy)carbonyl, carbamoyl, N-($C_1$ to $C_6$ alkyl)carbamoyl, N,N-di($C_1$ to $C_6$ alkyl)carbamoyl, phenyl, phenoxy, phenylthio, and the groups substituted phenyl, substituted phenoxy and substituted phenylthio wherein in each group the phenyl ring is substituted with from 1 to 3 substituents chosen from the group consisting of halogen, $C_1$ to $C_6$ alkyl, $C_1$ to $C_6$ haloalkyl, $C_1$ to $C_6$ alkoxy, nitro and cyano;

$R^1$ is chosen from the group consisting of hydrogen, $C_1$ to $C_6$ alkyl, $C_2$ to $C_6$ alkenyl, $C_2$ to $C_6$ alkoxyalkyl, $C_1$ to $C_6$ haloalkyl, acetyl, propionyl and $C_2$ and $C_6$ alkoxycarbonyl, $R^2$ is chosen from the group consisting of hydrogen, $C_1$ to $C_6$ alkyl, $C_2$ to $C_6$ alkenyl, $C_2$ to $C_6$ alkoxyalkyl and $C_1$ to $C_6$ haloalkyl, or $R^1$ and $R^2$ together may form a methylene, ethylidene, propylidene or isopropylidene group;

W is chosen from the group consisting of cyano, thiocarbamoyl,

and $CH_2Z$ wherein: G is chosen from the group consisting of hydroxy, mercapto, $C_1$ to $C_{10}$ alkoxy, $C_1$ to $C_{10}$ haloalkoxy, $C_2$ to $C_{10}$ alkenyloxy, $C_2$ to $C_{10}$ alkynyloxy, $C_1$ to $C_{10}$ alkylthio, $C_2$ to $C_{10}$ alkenylthio, $C_2$ to $C_{10}$ alkynylthio, $C_3$ to $C_7$ cycloalkoxy, $C_3$ to $C_7$ cycloalkoxy substituted with 1 or 2 $C_1$ to $C_4$ alkyl groups, phenoxy, phenylthio, benzyloxy, benzylthio, the group $C_1$ to $C_6$ alkoxy substituted with a substituent chosen from the group consisting of $C_1$ to $C_6$ alkoxy, amino, ammonio, cyano, N-($C_1$ to $C_6$ alkyl)amino, N,N-di($C_1$ to $C_6$ alkyl)amino and N,N,N-tri($C_1$ to $C_6$ alkyl)ammonio, the groups phenoxy, phenylthio, benzyloxy and benzylthio wherein in each group the phenyl ring is substituted with from 1 to 3 substituents chosen from the group consisting of halogen, nitro, cyano, $C_1$ to $C_6$ alkyl, $C_1$ to $C_6$ haloalkyl and $C_1$ to $C_6$ alkoxy, the group OM wherein M is the cation of an inorganic or organic base, the group $-NHSO_2R^3$ wherein $R^3$ is chosen from $C_1$ to $C_{10}$ alkyl and $C_1$ to $C_6$ haloalkyl, the group $-NR^4R^5$ wherein $R^4$ and $R^5$ are independently chosen from the group consisting of hydrogen, $C_1$ to $C_6$ alkyl, phenyl and benzyl or $R^4$ and $R^5$ together form a heterocyclic ring, and the group $-O-N=R^{10}$ wherein $R^{10}$ is a $C_1$ to $C_{10}$ alkylidene group;

Z is chosen from the group consisting of halogen, hydroxy, mercapto, $C_1$ to $C_{10}$ alkoxy, $C_1$ to $C_{10}$ haloalkoxy, $C_1$ to $C_{10}$ alkylthio and the group $-NR^4R^5$ wherein $R^4$ and $R^5$ are as hereinbefore defined;

X is chosen from oxygen and sulfur;

Y is chosen from oxygen, sulfur and the group $NR^6$ wherein $R^6$ is chosen from hydrogen, $C_1$ to $C_{10}$ alkyl, $C_2$ to $C_{10}$ alkenyl, $C_2$ to $C_{10}$ alkynyl, $C_2$ to $C_{10}$ alkoxyalkyl, cyanomethylene, $C_1$ to $C_6$-(alkoxy)carbonylmethylene, $C_1$ to $C_{10}$ haloalkyl, formyl, $C_2$ to $C_{10}$ alkanoyl, phenyl, benzyl, benzoyl, and the groups phenyl, benzyl and benzoyl wherein in each group the phenyl ring is substituted with from 1 to 3 substituents chosen from the group consisting of halogen, $C_1$ to $C_6$ alkyl, $C_1$ to $C_6$ halo-alkyl, $C_1$ to $C_6$ alkoxy, nitro and cyano;

k is chosen from 0 and 1; and n is 0, 1 or 2.

The compounds of formula I wherein $R^1$ and $R^2$ are not the same, are optically active and the present invention also includes the individual stereo isomers of such compounds, and mixtures of those stereo isomers in addition to the racemic mixture of stereo isomers. When W is the group

wherein G is the group OM and M is the cation of an inorganic or organic base, suitable inorganic bases include the alkali and alkaline earth metal hydroxides and carbonates, and ammonia and suitable organic bases include amines of the formula $NR^7R^8R^9$ wherein $R^7$, $R^8$ and $R^9$ are independently chosen from the group consisting of hydrogen, $C_1$ to $C_6$ alkyl, $C_1$ to $C_6$ hydroxyalkyl, phenyl and benzyl.

When W is chosen from the group

and $-CH_2Z$ wherein G or Z is the group $-NR^4R^5$ and $R^4$ and $R^5$ together form a heterocyclic ring, suitable heterocyclic groups include 1-pyrrolyl, 1-imidazolyl, 1-pyrazolyl, 1-pyrrolidinyl, 1-imidazolidinyl, 1-pyrazolindinyl, 1-piperidyl, 1-piperazinyl and 4-morpholinyl.

Preferred A, B, D, E, J, U and V include hydrogen, halogen, $C_1$ to $C_6$ alkyl, $C_1$ to $C_6$ haloalkyl, $C_1$ to $C_6$ alkoxy, $C_1$ to $C_6$ alkylthio, nitro and cyano.

Preferred $R^1$ and $R^2$ include hydrogen and $C_1$ to $C_6$ alkyl.

Preferred W is the group

The specific nature of G is not narrowly critical and therefore the group

may be a free carboxylic acid or a derivative thereof such as an acid salt, acid ester, acid amide, acid sulfonamide or acid oxime ester. Preferred G include hydroxy, $C_1$ to $C_{10}$ alkoxy, $C_1$ to $C_{10}$ haloalkoxy $C_2$ to $C_{10}$ alkenyloxy, $C_2$ to $C_{10}$ alkynyloxy, $C_1$ to $C_{10}$ alkylthio, $C_2$ to $C_{10}$ alkenylthio, $C_2$ to $C_{10}$ alkynylthio, cyclohexyloxy, phenoxy, benzyloxy, the group $C_1$ to $C_{10}$ alkoxy substituted with a substituent chosen from the group consisting of $C_1$ to $C_6$ alkoxy, amino, N-($C_1$ to $C_6$ alkyl)amino, N,N-di($C_1$ to $C_6$ alkyl)amino, N,N,N-tri($C_1$ to $C_6$ alkyl)ammonio, the group $-NR^4R^5$ wherein $R^4$ and $R^5$ are independently chosen from hydrogen, $C_1$ to $C_6$ alkyl, benzyl and phenyl, the group OM wherein M is an alkali metal ion, alkaline earth metal ion or an ammonium ion $HN^{\oplus}R^7R^8R^9$ wherein $R^7$, $R^8$ and $R^9$ are independently chosen from the group consisting of hydrogen, $C_1$ to $C_6$ alkyl, $C_1$ to $C_6$ hydroxyalkyl, phenyl and benzyl, the group $-NHSO_2R^3$ wherein $R^3$ is $C_1$ to $C_6$ alkyl, and the group $-O-N=R^{10}$ wherein $R^{10}$ is a $C_1$ to $C_{10}$ alkylidene group. More preferred G include hydroxy, $C_1$ to $C_{10}$ alkoxy, $C_2$ to $C_{10}$ alkenyloxy, $C_2$ to $C_{10}$ alkynyloxy, $C_1$ to $C_{10}$ alkylthio and the group OM wherein M is an alkali metal ion or alkaline earth metal ion.

Preferred X is oxygen.

Preferred Y include oxygen and the group $NR^6$ wherein $R^6$ is chosen from hydrogen, $C_1$ to $C_6$ alkyl, $C_2$ to $C_{10}$ alkenyl and $C_2$ to $C_{10}$ alkynyl.

Preferred n include 0 or 2.

Examples of the compounds embraced by the invention include:

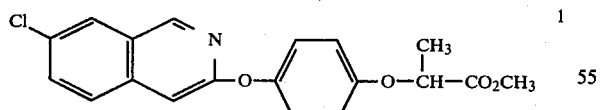

1

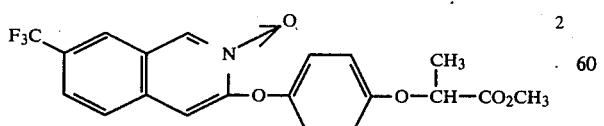

2

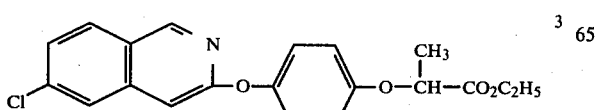

3

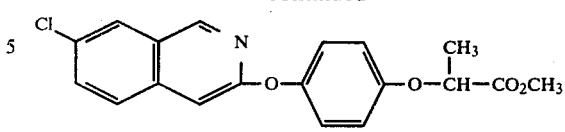

4

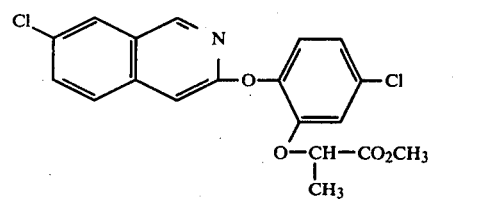

5

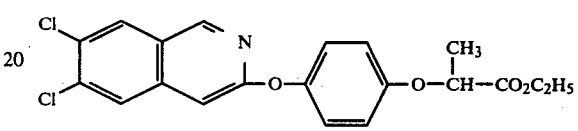

6

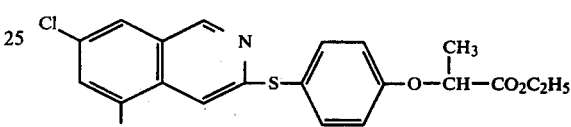

7

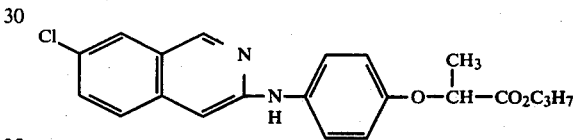

8

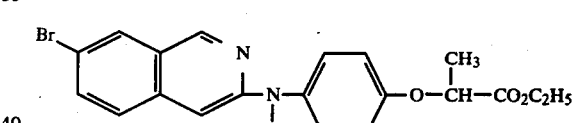

9

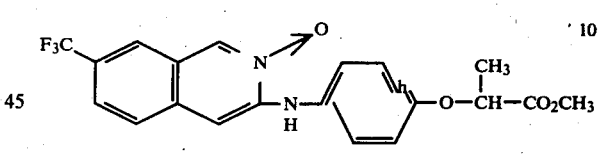

10

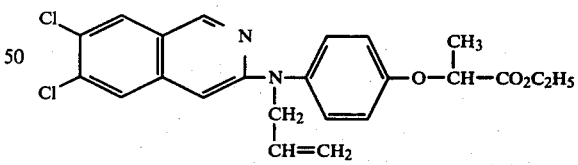

11

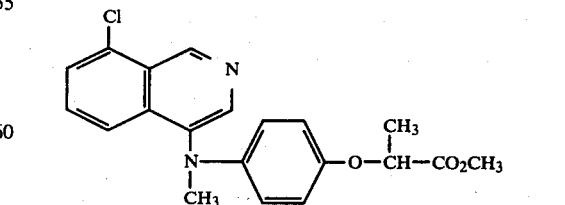

12

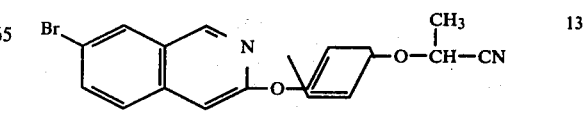

13

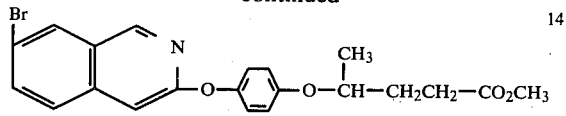

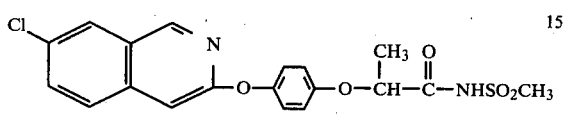

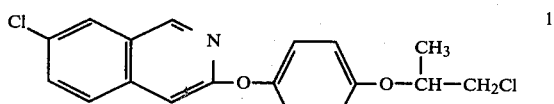

Particular compounds of the invention are detailed in Tables 1, 2 and 3 below.

TABLE 1

| Compound No | A,B,D,E | J | Y | R¹ | G |
|---|---|---|---|---|---|
| 17 | H | 3-Cl | O | H | $OC_2H_5$ |
| 18 | H | H | O | H | $OC_2H_5$ |
| 19 | H | 3-$CH_3$ | O | H | $OC_2H_5$ |
| 20 | 5-$NO_2$ | 3-Cl | O | H | $OC_2H_5$ |
| 21 | 5-$NO_2$ | 3-Cl | O | $CH_3$ | $OC_2H_5$ |
| 22 | H | 3-Cl | O | H | OH |
| 30 | H | 3-Cl | NH | $CH_3$ | $OC_2H_5$ |
| 76 | 5-$NO_2$ | 3-$CH_3$ | O | $CH_3$ | $OC_2H_5$ |

TABLE 2

| Compound No | A,B,D,E | J | Y | G |
|---|---|---|---|---|
| 23 | 7-Cl | 1-Cl | $NCH_3$ | $OC_2H_5$ |
| 24 | 7-Cl | H | $NCH_3$ | $OC_2H_5$ |

TABLE 2-continued

| Compound No | A,B,D,E | J | Y | G |
|---|---|---|---|---|
| 25 | H | 1-Cl | $NCH_3$ | $OC_2H_5$ |
| 26 | H | H | $NCH_3$ | $OC_2H_5$ |
| 28 | H | H | O | $OC_2H_5$ |
| 29 | H | 1-Cl | O | $OC_2H_5$ |
| 31 | H | 1-Cl | NH | $OC_2H_5$ |
| 33 | 4-Cl | 1-Cl | $NCH_3$ | $OC_2H_5$ |
| 34 | 7-Cl | H | O | $OC_2H_5$ |
| 35 | 4,7-$Cl_2$ | 1-Cl | $NCH_3$ | $OC_2H_5$ |
| 36 | 4-Cl | H | $NCH_3$ | $OC_2H_5$ |
| 37 | 7-Cl | 1-Cl | O | $OC_2H_5$ |
| 38 | H | 1-Br | $NCH_3$ | $OC_2H_5$ |
| 39 | 7-Cl | 1-Br | $NCH_3$ | $OC_2H_5$ |
| 40 | 7-Cl | 4-Cl | $NCH_3$ | $OC_2H_5$ |
| 41 | 7-$CH_3$ | 1-Cl | $NCH_3$ | $OC_2H_5$ |
| 42 | 7-Br | 1-Cl | $NCH_3$ | $OC_2H_5$ |
| 43 | H | 1-$OCH_3$ | $NCH_3$ | OH |
| 44 | 7-Cl | 1-$OCH_3$ | $NCH_3$ | $OCH_3$ |
| 45 | 7-F | 1-Cl | $NCH_3$ | $OC_2H_5$ |
| 46 | 6-Cl | 1-Cl | $NCH_3$ | $OC_2H_5$ |
| 47 | 6-Cl | H | $NCH_3$ | $OC_2H_5$ |
| 48 | 7-Cl | 1-Cl | NH | $OC_2H_5$ |
| 49 | 7-Cl | 1-Cl | $NC_2H_5$ | $OC_2H_5$ |
| 50 | 7-Cl | 1-Cl | $NCH_3$ | OH |
| 51 | 7-Cl | 1-Cl | $NCH_3$ | $OCH_2CH_2N(CH_3)_2$ |
| 52 | 7-CN | 1-Cl | $NCH_3$ | $OC_2H_5$ |
| 53 | 7-Cl | 1,4-$Cl_2$ | $NCH_3$ | $OCH_2CH_2N(CH_3)_2$ |
| 54 | 7-Cl | 1-Cl | $NCH_3$ | $O^\ominus Na^\oplus$ |
| 55 | 7-Cl | 1-Cl | $NCH_3$ | $O-N=CH(CH_3)_2$ |
| 56 | 7-Cl | 1-Cl | $NCH_3$ | $S(CH_2)_3CH_3$ |
| 57 | 7-Cl | 1-Cl | $NCH_3$ | $OCH_2CH_2\overset{\oplus}{N}(CH_3)_3 I^\ominus$ |
| 58 | 7-Cl | 1-Cl | $NCH_3$ | $N(CH_2CH_2CH_3)_2$ |
| 59 | H | 1-CN | $NCH_3$ | $OC_2H_5$ |
| 60 | 6,7-$Cl_2$ | 1-Cl | $NCH_3$ | $OC_2H_5$ |
| 61 | 7-Cl | 1-CN | $NCH_3$ | $OC_2H_5$ |
| 62 | 7-F | 1-F | $NCH_3$ | $OC_2H_5$ |
| 63 | 6-F | 1-Cl | $NCH_3$ | $OC_2H_5$ |
| 64 | 7-F | H | O | $OC_2H_5$ |
| 65 | 7-Cl | 1-$SCH_3$ | $NCH_3$ | $OC_2H_5$ |
| 66 | 7-Cl | 1-F | $NCH_3$ | $OC_2H_5$ |
| 67 | 7-Cl, 6-F | 1-Cl | $NCH_3$ | $OC_2H_5$ |
| 69 | 7-Cl, 6-CN | 1-Cl | $NCH_3$ | $OC_2H_5$ |
| 70 | 7-$OCH_3$ | 1-Cl | $NCH_3$ | $OC_2H_5$ |
| 71 | 7-F | 1-Cl | $NCH_3$ | $OCH_3$ |
| 72 | 7-F | H | $NCH_3$ | $OC_2H_5$ |
| 73 | 7-Cl | 1-Cl | $NCH_3$ | $OCH_2CH_2CH_3$ |
| 74 | 7-Cl | 1-Cl | $NCH_3$ | $O(CH_2)_3CH_3$ |
| 75 | 7-Cl | 1-Cl | $NCH_3$ | $OCH_3$ |

TABLE 3

| Compound No | Structure |
|---|---|
| 27 | (isoquinoline N-oxide structure with $O-C_6H_4-O-CH(CH_3)-CO_2C_2H_5$ substituent) |

TABLE 3-continued

| Compound No | Structure |
|---|---|
| 32 | 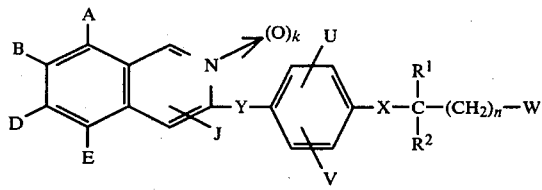 |
| 68 | 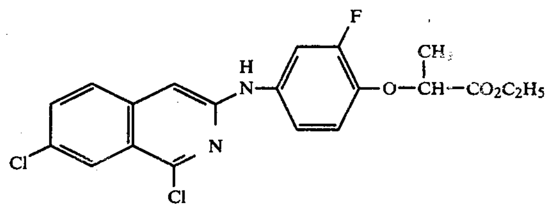 |
| 77 | 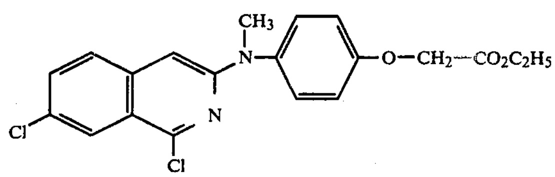 |
| 78 | 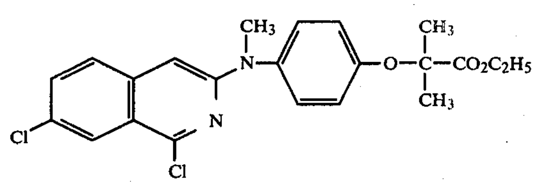 |

Preferred compounds of formula I are those 3-isoquinolyl compounds in which the phenyl ring is 1,4-substituted, that is compounds of formula II

II

This includes compounds of Formula II wherein A, E, V and $R^2$ are hydrogen; B and D are independently chosen from the group consisting of hydrogen, halogen, methyl and cyano; J is chosen from the group consisting of hydrogen, halogen and cyano; U is chosen from hydrogen and halogen; $R^1$ is methyl; W is the group

wherein G is chosen from the group consisting of hydroxy, $C_1$ to $C_6$ alkoxy and the group OM wherein M is an alkali metal ion; X is oxygen; Y is chosen from oxygen and the group $NR^6$ wherein $R^6$ is chosen from hydrogen, methyl and ethyl; and k and n are 0.

A preferred group of such compounds are those wherein A, D, E, U, V and $R^2$ are hydrogen; B and J are independently chosen from hydrogen and halogen; $R^1$ is methyl; W is the group

wherein G is chosen from the group consisting of hydroxy, $C_1$ to $C_6$ alkoxy and the group OM wherein M is an alkali metal ion; X is oxygen; Y is chosen from oxygen and the group $NR^6$ wherein $R^6$ is chosen from hydrogen or methyl; and k and n are both 0.

Within the group of compounds mentioned in the preceding paragraph are those compounds wherein A, D, E, J, U, V and $R^2$ are hydrogen; B is chosen from fluorine, chlorine and bromine; $R^1$ is methyl; W is the group

wherein G is chosen from the group consisting of hydroxy, $C_1$ to $C_6$ alkoxy and the group OM wherein M is sodium or potassium; X and Y are both oxygen; and k and n are both 0.

Alternatively the compounds may be of Formula II wherein A, D, E, J, U, V and $R^2$ are hydrogen; B is chosen from fluorine, chlorine and bromine; $R^1$ is methyl; W is the group wherein G is chosen from the group consisting of hydroxy, $C_1$ to $C_6$ alkoxy and the group OM wherein M is sodium or potassium; X is oxygen; Y is the group $NR^6$ wherein $R^6$ is methyl; and k and n are both 0.

halides and acid amides may be adapted, without undue experimentation, to prepare compounds of the invention of formula Ia from compounds of the invention of formula Ib.

SCHEME A

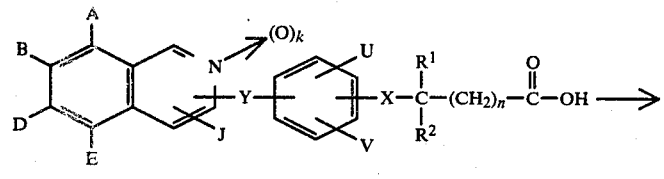

Ib

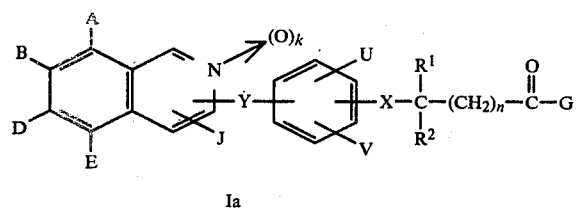

Ia

The compounds of the invention may be prepared by a variety of methods and in a further aspect the invention provides methods for the preparation of the compounds of formula I.

Nitriles of the invention of formula Ic (I; W=—C≡N) may be prepared, for example, from the acid amide of formula Id (I; W=—CONH$_2$) (SCHEME B).

SCHEME B

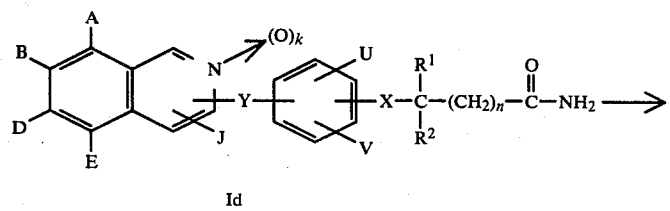

Id

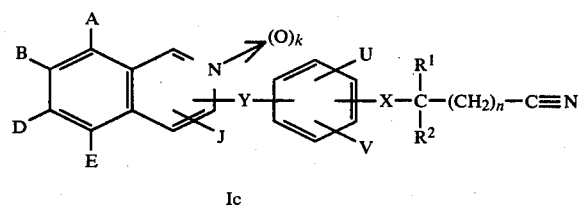

Ic

Compounds of formula Ia (I; W=

—C—G)

wherein G is not hydroxy may be prepared from the acid of formula Ib (I; W=—CO$_2$H) by, for example, neutralisation of the acid with a base to give an acid salt, esterification of the acid with an alcohol, thiol, phenol or thiophenol to give an acid ester, or reaction of the acid (or acid halide derivative thereof) with an amine to give an amide (SCHEME A). Processes known in the art for the preparation of acid salts, acid esters, acid Alcohols of the invention of formula Ie (I; W=—CH$_2$OH) may be prepared from the acid or acid esters of formula If (I; W=

—C—G wherein G=OH or O-alkyl) by reduction (SCHEME C). Processes known in the art for the reduction of acids or acid esters to alcohols, for example lithium aluminium hydride reduction, may be adapted, without undue experimentation, to prepare alcohols of the invention of formula Ie from esters of the invention of formula If.

SCHEME C

SCHEME C

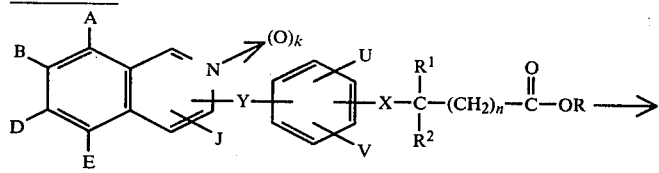

If

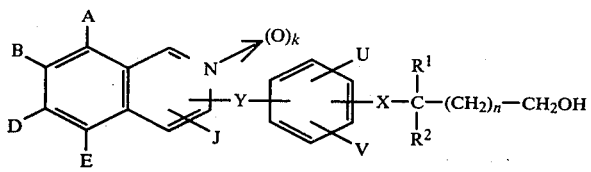

Ie

Alkyl halides of the invention of formula Ig (I; W=—CH₂-halogen) may be prepared from alcohols of formula Ie (I; W=—CH₂OH) by halogenation. Processes known in the art for the conversion of alcohols to alkyl halides, for example halogenation with reagents such as thionyl chloride, may be adapted, without undue experimentation, to prepare alkyl halides of the invention of formula Ig from alcohols of the invention of formula Ie.

Ethers of the invention of formula Ih (I; W=—CH₂OR) may be prepared from alcohols of formula Ie (I; W=—CH₂OH) by alkylation. Processes known in the art for the conversion of alcohols to ethers, for example by reaction with alkyl halides using the Williamson ether synthesis, may be adapted, without undue experimentation, to prepare ethers of the invention of formula Ih from alcohols of the invention of formula Ie.

Ethers (thioethers) of the invention of formula Ih (Ii) [I; W=—CH₂OR(—CH₂SR)] may be prepared from alkyl halides of formula Ig (I; W=CH₂-halogen) by alkoxylation (thioalkoxylation). Processes known in the art for the conversion of alkyl halides to ethers (thioethers), for example by reaction with alcohols (thiols) using the Williamson ether synthesis, may be adapted, without undue experimentation, to prepare ethers (thioethers) of the invention of formula Ih (Ii) from alkyl halides of the invention of formula Ig.

Amines of the invention of formula Ij (I; W=CH₂NR⁴R⁵) may be prepared from the alkyl halides of formula Ig (I; W=—CH₂-halogen) by amination or from the amides of formula Ik (I; W=

$$-\overset{O}{\underset{\|}{C}}-NR^4R^5)$$

by reduction. Processes known in the art for the conversion of alkyl halides to amines, for example by reaction with amines, and for the conversion of amides to amines, for example by reduction with agents such as lithium aluminium hydride, may be adapted without undue experimentation, to prepare amines of the invention of formula Ij from alkyl halides of the invention of formula Ig and from amides of the invention of formula Ik respectively.

N-oxides of the invention of formula I wherein k is 1 may be prepared from compounds of the invention of formula I wherein k is 0 by oxidation. Processes known in the art for the conversion of isoquinolines to isoquinoline N-oxides, for example oxidations using persulfates, peroxides, peracids or peresters, may be adapted, without undue experimentation, to prepare N-oxides of the invention.

Compounds of the invention of formula I in which Y is the group NR⁶ wherein R⁶ is not hydrogen may be prepared from compounds of the invention of formula I in which Y is the group NR⁶ wherein R⁶ is hydrogen by, for example, alkylation or acylation. Processes known in the art for the preparation of derivatives of secondary amines, for example alkylations with alkyl halides and acylations with acyl halides, may be adapted, without undue experimentation, to prepare the novel compounds of the invention wherein R¹ is not hydrogen.

Compounds of formula I wherein A, B, D, E, U, V, Y, X, R¹, R², J, W, k and n are as hereinbefore defined may be prepared by the condensation of a phenol or thiophenol of formula IX with a compound of formula X wherein hal is chlorine, bromine or iodine, preferably in the presence of an alkaline material; according to SCHEME D.

SCHEME D

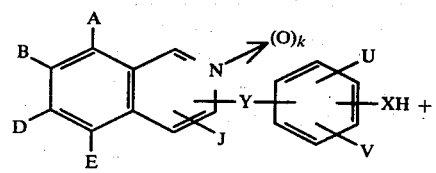

IX

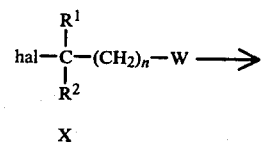

X

SCHEME D -continued

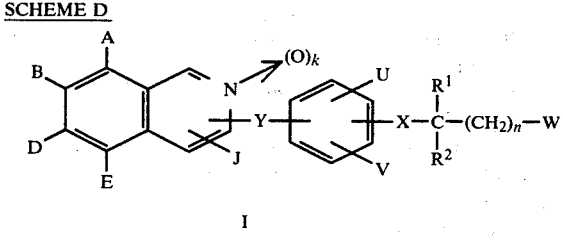

I

Compounds of formula I may also be prepared by:
(a) the condensation of the appropriate isoquinoline derivative of formula V, wherein L is a leaving group (for example, alkylsulfonyl, chlorine, bromine or iodine) with the appropriate compound of formula VI according to SCHEME E.

SCHEME E

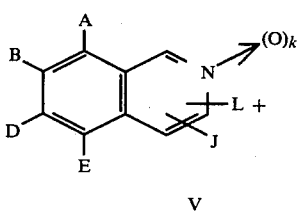

V

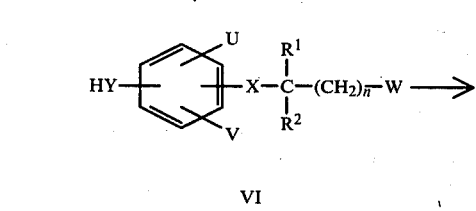

VI

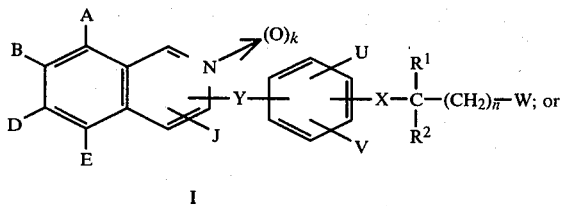

I (b) the following steps in sequence:
(i) the condensation of the appropriate isoquinoline derivative of formula V, wherein L is a leaving group (for example, alkylsulfonyl, chlorine, bromine or iodine) with the appropriate compound of formula VII, wherein Q is hydroxy, mercapto, $C_1$ to $C_6$ alkoxy or $C_1$ to $C_6$ alkylthio to give a compound of formula VIII wherein Q is hydroxy, mercapto, $C_1$ to $C_6$ alkoxy or $C_1$ to $C_6$ alkylthio;
(ii) the dealkylation of the compound of formula VIII prepared in step (i) above wherein Q is $C_1$ to $C_6$ alkoxy or $C_1$ to $C_6$ alkylthio to give a compound of formula IX; and
(iii) the condensation of the product of formula IX obtained in step (i) or step (ii) above with a compound of formula X according to the process described for SCHEME D above (Steps (i) and (ii) are shown in SCHEME F); or

SCHEME F

SCHEME F -continued

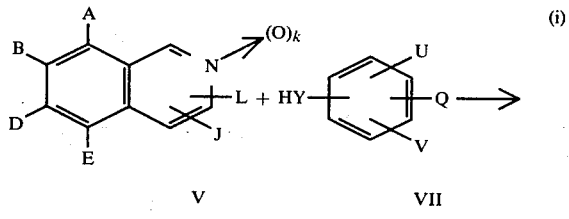

V        VII

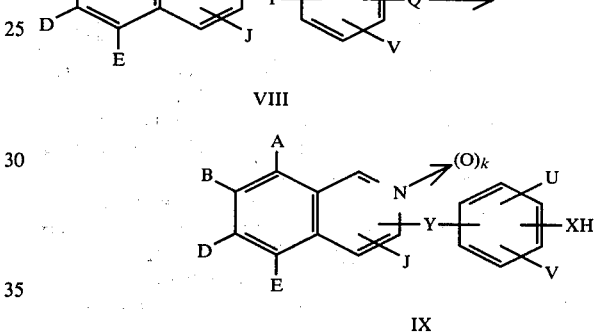

VIII

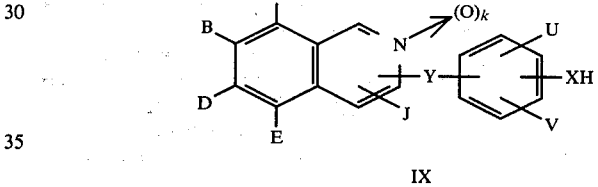

VIII

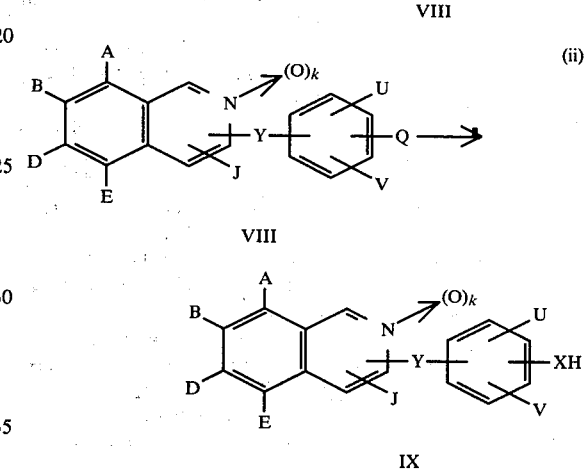

IX (c) the following steps in sequence:
(i) the condensation of the appropriate isoquinoline derivative of formula XI with the appropriate benzene derivative of formula XII wherein L is a leaving group (for example, alkylsulfonyl, chlorine, bromine or iodine) and Q is hydroxy, mercapto, $C_1$ to $C_6$ alkoxy or $C_1$ to $C_6$ alkylthio, to give a compound of formula VIII wherein Q is as hereinbefore defined;
(ii) the dealkylation of the compound of formula VIII prepared in step (i) above wherein Q is $C_1$ to $C_6$ alkoxy or $C_1$ to $C_6$ alkylthio, to give a compound of formula IX according to the process described for SCHEME F step (ii) above; and
(iii) the condensation of the product of formula IX obtained in step (i) or step (ii) above with a compound of formula X according to the process described for SCHEME D above (step (i) is shown in SCHEME G).

SCHEME G

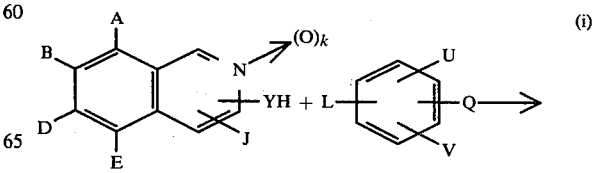

XI        XII

SCHEME G
-continued

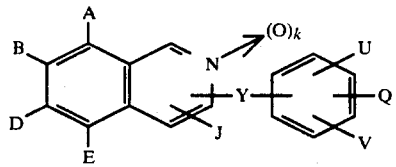

VIII

The condensation reaction illustrated in SCHEMES D, and E to G wherein Y is oxygen or sulfur, and outlined above are preferably carried out in the presence of an alkaline material. Suitable alkaline materials include alkali metal and alkaline earth metal hydroxides and carbonates such as, for example, sodium hydroxide, potassium hydroxide, sodium carbonate and potassium carbonate.

The condensation reactions illustrated in Schemes D to G and outlined above are also preferably carried out in the presence of a solvent. Suitable solvents include ketones such as, for example, acetone, methyl ethyl ketone and methyl isobutyl ketone, and dipolar aprotic solvents such as, for example, dimethylformamide, dimethylacetamide, dimethylsulfoxide, N-methylpyrrolidone, hexamethylphosphoramide and sulfolan.

The reaction conditions required to effect the condensation reactions illustrated in SCHEMES D, E, F, and G and outlined above vary according to the nature of the reactants and the solvent used. In general the reaction is facilitated by the application of heat and usually a reaction temperature in the range of 40° to 150° C. and reaction time of between 0.5 and 20 hours is satisfactory. However, higher or lower reaction temperatures and/or shorter or longer reaction times may be used if desired.

The dealkylation reactions illustrated in SCHEMES F and G and outlined in paragraphs (b) (ii) and (c) (ii) above may be effected using a variety of reagents known in the art. For example, aryl-alkyl ethers may be cleaved using reagents such as pyridine hydrochloride, hydriodic acid, hydrobromic acid, sodium thioethoxide in dimethylformamide, acetyl p-toluenesulphonate, sodium or potassium iodide in formic or acetic acid, lithium iodide in 2,4,6-collidine and boron tribromide. Reaction times and reaction conditions vary widely depending on the dealkylation agent used and the ether to be cleaved.

The reaction conditions generally employed when using the above "ether-cleavage" reagents are known to those skilled in the art and may be adapted without undue experimentation to effect the "ether-cleavage" reactions illustrated in SCHEMES F and G and outlined in paragraph (b) (ii) and (c) (ii) above.

The compounds of formula VIII

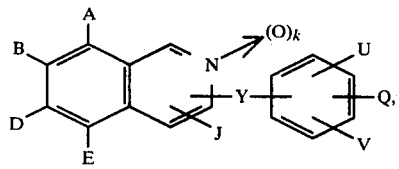

VIII which are useful intermediate in the preparation of compounds of formula I, are novel compounds. Therefore, in a further embodiment the invention provides compounds of formula VIII wherein A, B, D, E, J, k, Y, U, V and Q are as hereinbefore defined.

The compounds of formula I are active as herbicides and therefore, in a further aspect the invention provides a process for severely damaging or killing unwanted plants which process comprises applying to the plants, or to the growth medium of the plants, an effective amount of a compound of formula I as hereinbefore defined.

Generally speaking the compounds of formula I are herbicidally effective against a variety of plants. However, certain of the compounds of the invention are selectively active against monocotyledonous plants, dicotyledonous plants being relatively unaffected by rates of application of the compounds of the invention which are severely damaging or lethal to other plant species.

Moreover, certain of the compounds of formula I are selectively active within the group of monocotyledonous plants and may be used at a rate sufficient to kill or severly damage monocotyledonous weeds in a monocotyledonous cereal crop.

Therefore, in yet a further aspect the invention provides a process for selectively controlling the growth of weeds in crops which process comprises applying to the crop, or to the growth medium of the crop, a compound of formula I, as hereinbefore defined, in an amount sufficient to severely damage or kill the weeds but insufficient to damage the crop substantially.

The compounds of formula I may be applied directly to the plant (post-emergence application) or to the soil before the emergence of the plant (pre-emergence application). However, the compounds are, in general, more effective when applied to the plant post-emergence.

The compounds of formula I may be used on their own to inhibit the growth of, severely damage, or kill plants but are preferably used in the form of a composition comprising a compound of the invention in admixture with a carrier comprising a solid or liquid diluent. Therefore, in yet a further aspect the invention provides plant growth inhibiting, plant damaging, or plant killing compositions comprising a compound of formula I as hereinbefore defined and an inert carrier therefor.

Compositions according to the invention include both dilute compositions, which are ready for immediate use, and concentrated compositions, which require to be diluted before use, usually with water. Preferably the compositions contain from 0.01% to 90% by weight of the active ingredient. Dilute compositions ready for use preferably contain from 0.01 to 2% of active ingredient, while concentrated compositions may contain from 20 to 90% of active ingredient, although from 20 to 70% is usually preferred.

The solid compositions may be in the form of granules, or dusting powders wherein the active ingredient is mixed with a finely divided solid diluent, eg kaolin, bentonite, kieselguhr, dolomite, calcium carbonate, talc, powdered magnesia, Fuller's earth and gypsum. They may also be in the form of dispersible powders or grains, comprising a wetting agent to facilitate the dispersion of the powder or grains in liquid. Solid compositions in the form of a powder may be applied as foliar dusts.

Liquid compositions may comprise a solution or dispersion of an active ingredient in water optionally containing a surface-active agent, or may comprise a solution or dispersion of an active ingredient in a waterimmiscible organic solvent which is dispersed as droplets in water.

Surface-active agents may be of the cationic, anionic, or non-ionic type. The cationic agents are, for example, quaternary ammonium compounds (eg cetyltrimethlammonium bromide). Suitable anionic agents are soaps; salts of aliphatic mono esters of sulphuric acid, for example sodium lauryl sulphate; and salts of sulphonated aromatic compounds, for example sodium dodecylbenzenesulphonate, sodium, calcium, and ammonium lignosulphonate, butylnaphthalene sulphonate, and a mixture of the sodium salts of diisopropyl- and triisopropylnaphthalenesulphonic acid. Suitable non-ionic agents are the condensation products of ethylene oxide with fatty alcohols such as oleyl alcohol and cetyl alcohol, or with alkylphenols such as octyl- or nonyl-phenol or octylcresol. Other non-ionic agents are the partial esters derived from long chain fatty acids and hexitol anhydrides, for example sorbitan monolaurate; the condensation products of the partial ester with ethylene oxide; and the lecithins.

The aqueous solutions or dispersions may be prepared by dissolving the active ingredient in water or an organic solvent optionally containing wetting or dispersing agent(s) and then, when organic solvents are used, adding the mixture so obtained to water optionally containing wetting or dispersing agent(s). Suitable organic solvents include, for example, ethylene dichloride, isopropyl alcohol, propylene glycol, diacetone alcohol, toluene, kerosene, methylnaphthalene, the xylenes and trichloroethylene.

The compositions for use in the form of aqueous solutions or dispersions are generally supplied in the form of a concentrate containing a high proportion of the active ingredient, and the concentrate is then diluted with water before use. The concentrates are usually required to withstand storage for prolonged periods and after such storage, to be capable of dilution with water to form aqueous preparations which remain homogeneous for a sufficient time to enable them to be applied by conventional spray equipment. Concentrates conveniently contain 20-90%, preferably 20-70%, by weight of the active ingredient(s). Dilute preparations ready for use may contain varying amounts of the active ingredient(s) depending upon the intended purpose; amounts of 0.01% to 10.0% and preferably 0.1% to 2%, by weight of active ingredient(s) are normally used.

A preferred form of concentrated composition comprising the active ingredient which has been finely divided and which has been dispersed in water in the presence of a surface-active agent and a suspending agent. Suitable suspending agents are hydrophilic colloids and include, for example, polyvinylpyrrolidone and sodium carboxymethylcellulose, and the vegetable gums, for example gum acacia and gum tragacanth. Preferred suspending agents are those which impaart thixotropic properties to, and increase the viscosity of the concentrate. Examples of preferred suspending agents include hydrated colloidal mineral silicates, such as montmorillonite, beidellite, nontronite, hectorite, saponite, and saucorite. Bentonite is especially preferred. Other suspending agents include cellulose derivatives and polyvinyl alcohol.

The rate of application of the compounds of the invention will depend on a number of factors including, for example, the compound chosen for use, the identity of the plants whose growth is to be inhibited the formulations selected for use and whether the compound is to be applied for foliage or root uptake. As a general guide, however, an application rate of from 0.005 to 20 kilograms per hectare is suitable while from 0.1 to 10 kilograms per hectare may be preferred.

The compositions of the invention may comprise, in addition to one or more compounds of the invention, one or more compounds not of the invention but which possess biological activity. For example, as hereinbefore indicated the compounds of the invention are in general substantially more effective against monocotyledonous plants or grass species than against dicotyledonous plants or broad-leaved species. As a result, in certain applications the herbicidal use of the compounds of the invention alone may be sufficient to protect a crop. Accordingly in yet a still further embodiment the invention provides a herbicidal composition comprising a mixture of at least one herbicidal compound of formula I as hereinbefore defined with at least one other herbicide.

The other herbicide may be any herbicide not having the formula I. It will generally be a herbicide having a complementary action. For example, one preferred class is of mixtures comprising a herbicide active against broad-leaved weeds. A second preferred class is of mixtures comprising a contact herbicide.

Examples of useful complementary herbicides include:

A. benzo-2,1,3-thiadiazin-4-one-2,2-dioxides such as 3-isopropylbenzo-2,1,3-thiadiazin-4-one-2,2-dioxide (common name bentazon);

B. hormone herbicides and in particular the phenoxyalkanoic acids such as 4-chloro-2-methylphenoxy acetic acid (common name MCPA), 2-(2,4-dichlorophenoxy)propionic acid (common name dichlorprop), 2,4,5-trichlorophenoxyacetic acid (common name 2,4,5-T), 4-(4-chloro-2-methylphenoxy)butyric acid (common name MCPB), 2,4-dichlorophenoxyacetic acid (common name 2,4-D), 4-(2,4-dichlorophenoxy)butyric acid (common name 2,4-DB), 2-(4-chloro-2-methylphenoxy)propionic acid (common name mecoprop), and their derivatives (eg salts, esters, amides and the like);

C. 3-[4-(4-halophenoxy)phenyl]-1,1-dialkylureas such as 3-[4-(4-chlorophenoxy)phenyl]-1,1-dimethylurea (common name chloroxuron);

D. dinitrophenols and their derivatives (eg acetates) such as 2-methyl-4,6-dinitrophenol (common name DNOC), 2-tertiarybutyl-4,6-dinitrophenol (common name dinoterb), 2-secondarybutyl-4,6-dinitrophenol (common name dinoseb) and its ester dinoseb acetate;

E. dinitroaniline herbicides such as N',N'-diethyl-2,6-dinitro-4-trifluoromethyl-m-phenylenediamine (common name dinitramine), 2,6-dinitro-N,N-dipropyl-4-trifluoromethylaniline (common name trifluralin) and 4-methylsulfonyl-2,6-dinitro-N,N-dipropylaniline (common name nitralin);

F. phenylurea herbicides such as N'-(3,4-dichlorophenyl)-N,N-dimethylurea (common name diuron) and N,N-dimethyl-N'-[3-(trifluoromethyl)phenyl]urea (common name fluometuron);

G. phenylcarbamoyloxyphenylcarbamates such as 3-[(methoxycarbonyl)amino]phenyl (3-methylphenyl)carbamate (common name phenmedipham) and 3-[(ethoxycarbonyl)amino]phenyl phenylcarbamate (common name desmedipham);

H. 2-phenylpyrdazin-3-ones such as 5-amino-4-chloro-2-phenylpyridazin-3-one (common name pyrazon);

I. uracil herbicides such as 3-cyclohexyl-5,6-trimethyleneuracil (common name lenacil), 5-bromo-3-sec-butyl-6-methyluracil (common name bromacil) and 3-tert-butyl-5-chloro-6-methyluracil (common name terbacil);

J. triazine herbicides such as 2-chloro-4-ethylamino-6-(iso-propylamino)-1,3,5-triazine (common name atrazine), 2-chloro-4,6-di(ethylamino)-1,3,5-triazine (common name simazine) and 2-azido-4-(iso-propylamino)-6-methylthio-1,3,5-triazine (common name aziprotryne);

K. 1-alkoxy-1-alkyl-3-phenylurea herbicides such as 3-(3,4-dichlorophenyl)-1-methoxy-1-methylurea (common name linuron), 3-(4-chlorophenyl)-1-methoxy-1-methylurea (common name monolinuron) and 3-(4-bromo-4-chlorophenyl)-1-methoxy-1-methylurea (common name chlorobromuron);

L. thiolcarbamate herbicides such as S-propyl dipropylthiocarbamate (common name verolate);

M. 1,2,4-triazin-5-one herbicides such as 4-amino-4,5-dihydro-3-methyl-6-phenyl-1,2,4-triazine-5-one (common name metamitron) and 4-amino-6-tert-butyl-4,5-dihydro-3-methylthio-1,3,4-triazin-5-one (common name metribuzin);

N. benzoic acid herbicides such as 2,3,6-trichlorobenzoic acid (common name 2,3,6-TBA), 3,6-dichloro-2-methoxybenzoic acid (common name dicamba) and 3-amino-2,5-dichlorobenzoic acid (common name chloramben).

O. anilide herbicides such as N-butoxymethyl-α-chloro-2',6'-diethylacetanilide (common name butachlor), the corresponding N-methoxy compound (common name alachlor), the corresponding N-iso-propyl compound (common name propachlor) and 3',4'-dichloropropionanilide (common name propanil);

P. dihalobenzonitrile herbicides such as 2,6-dichlorobenzonitrile (common name dichlobenil), 3,5-dibromo-4-hydroxybenzonitrile (common name bromoxynil) and 3,5-diiodo-4-hydroxybenzonitrile (common name ioxynil).

Q. haloalkanoic herbicides such as 2,2-dichlorpropionic acid (common name dalapon), trichloroacetic acid (common name TCA) and salts thereof;

R. diphenylether herbicides such as 4-nitrophenyl 2-nitro-4-trifluoromethylphenyl ether (common name fluorodifen), methyl 5-(2,4-dichlorophenoxy)-2-nitrobenzoate (common name bifenox), 2-nitro-5-(2-chloro-4-trifluoromethylphenoxy)benzoic acid, 2-chloro-4-trifluoromethylphenyl 3-ethoxy-4-nitrophenyl ether and the compounds disclosed in European Patent publication No 3,416; and S. miscellaneous herbicides including N,N-dimethyldiphenylacetamide (common name diphenamid), N-(1-naphthyl)phthalamic acid (common name naptalam) and 3-amino-1,2,4-triazole.

Examples of useful contact herbicides include:

T. bipyridylium herbicides such as those in which the active entity is the 1,1'-dimethyl-4,4'-dipyridylium ion (common name paraquat) and those in which the active entity is the 1,1'-ethylene-2,2'-dipyridylium ion (common name diquat), U. organoarsenical herbicides such as monosodium methanearsonate (common name MSMA); and V. amino acid herbicides such as N-(phosphonomethyl)glycine (common name glyphosate) and its salts and esters.

The invention is now illustrated by, but in no way limited to, the following Examples.

EXAMPLE 1

Ethyl 4-(3-chloro-1-isoquinolyloxy)phenoxyacetate (17)

A mixture of ethyl 4-hydroxyphenoxyacetate (1.0 g), 1,3-dichloroisoquinoline (1.0 g), anhydrous potassium carbonate (0.7 g) and dry dimethylformamide (10 ml) was heated, with stirring, at a temperature of 120°–130° C. for a period of 3 hours. The solvent was removed by distillation under reduced pressure and the residue was treated with water. The aqueous mixture was extracted with a mixture of acetone and chloroform and the solvents were removed from the organic extract by distillation under reduced pressure. The residue was chromatographed over silica gel with chloroform elution to give ethyl 4-(3-chloro-1-isoquinolyloxy)phenoxyacetate (1.2 g), mp 97° C. The assigned structure was confirmed by proton magnetic resonance spectroscopy, mass spectrometry and elemental analysis.

EXAMPLE 2

The following compounds were prepared from the appropriate 1-chloroisoquinoline and ethyl 4-hydroxyphenoxycarboxylate following essentially the same process as that described in Example 1 above: ethyl 4-(1-isoquinolyloxy)phenoxyacetate (18), mp 70° C.; ethyl 4-(3-methyl-1-isoquinolyloxy)phenoxyacetate (19), mp 101° C.; ethyl 4-(3-chloro-5-nitro-1-isoquinolyloxy)phenoxyacetate (20), mp 129° C.; ethyl 2-[4-(3-chloro-5-nitro-1-isoquinolyloxy)phenoxy]propionate (21), mp 103°–104° C.; and ethyl 2-[4-(3-methyl-5-nitro-1-isoquinolyloxy)phenoxy]propionate (76) 101° C. The assigned structures were confirmed by proton magnetic resonance spectroscopy and mass spectrometry.

EXAMPLE 3

4-(3-Chloro-1-isoquinolyloxy)phenoxyacetic acid (22) was prepared by alkaline hydrolysis (aqueous NaOH) of ethyl 4-(3-chloro-1-isoquinolyloxy)phenoxyacetic acid (17) and acidification of the alkaline reaction mixture to recover the acid. The product had a melting point of 186° C. and its structure was confirmed by proton magnetic resonance spectroscopy and mass spectroscopy.

EXAMPLE 4

Ethyl 2-{4-[N-(1,7-dichloroisoquinolin-3-yl)-N-methylamino]phenoxy}propionate (23)

(a) 6-Nitrophthalide (14.0 g; J A Houbion, J A Miles and J A Paton, *Organic Preparations and Procedures International*, 11 (1), 27, 1979) in solution in acetic acid was hydrogenated over a palladium on carbon catalyst to give 6-aminophthalide (12.0 g; W R Vaughan and S L Baird, *J. Amer. Chem. Soc.* 68, 1314, 1946). 6-Aminophthalide (10.0 g) was converted, via the diazonium salt intermediate, to 6-chlorophthalide (8.5 g; J Tirouflet, *Bull. soc. sci.* Bretagne Spec. No 26, 7, 1951).

A mixture of 6-chlorophthalide (2.0 g) and potassium cyanide (2.0 g) was stirred at a temperature of 180° C. for a period of 4 hours. The solid was cooled, dissolved in water and the solution was acidified with concentrated hydrochloric acid. The dark brown solid was collected, washed with water and dried. The crude solid was dissolved in ethyl acetate, the solution was treated with charcoal, filtered, and the solvent was evaporated to give 4-chloro-2-carboxyphenylacetonitrile (1.70 g) as pale yellow crystals mp 120° C.

A mixture of 4-chloro-2-carboxyphenylacetonitrile (8.0 g) and N-methyl-4-hydroxyaniline (10.0 g) and chlorobenzene was heated under reflux for a period of 2 hours. The mixture was cooled and the product which crystallised was collected by filtration. The solid was washed several times with acetone to give 4-[N-(7-chloro-1-hydroxyisoquinolin-3-yl)-N-methylamino]phenol (8.57 g) mp 266° C.

A mixture of 4-[N-(7-chloro-1-hydroxyisoquinolin-3-yl)-N-methylamino]phenol (4.0 g) and phosphorus oxychloride was heated under reflux for approximately 10 minutes at which stage a clear solution had been obtained. The mixture was cooled and poured into ice-water. The precipitated solid was collected and purified by column chromatography over silica gel (eluant dichloromethane/ethyl acetate; 90:10) to give 4-[N-(1,7-dichloroisoquinolin-3-yl)-N-methylamino]phenol (2.57 g) as a yellow crystalline solid mp 124° C.

(b) A mixture of ethyl 2-bromopropionate (1.6 g), 4-[N-(1,7-dichloroisoquinolin-3-yl)-N-methylamino]phenol (2.76 g), anhydrous potassium carbonate (1.19 g) and methyl ethyl ketone was heated under reflux for a period of 3 hours. The mixture was cooled, washed with water and was dried over anhydrous magnesium sulfate. The solvent was removed by distillation under reduced pressure to give an oil which was purified by column chromatography over silica gel (eluant dichloromethane) to give ethyl 2-{4-[N-(1,7-dichloroisoquinolin-3-yl)-N-methylamino]phenoxy}propionate (3.10 g) as a yellow oil which crystallised from ethanol, mp 86° C. The assigned structure was confirmed by proton magnetic resonance spectroscopy and mass spectrometry. Proton magnetic resonance spectrum (CDCl$_3$; δ in ppm): 1.3 (3H, t); 1.65 (3H, d); 3.45 (3H, s); 4.25 (2H, q); 4.75 (1H, q); 6.40 (1H, s); 6.85–7.35 (6H, m); 8.00 (1H, s).

EXAMPLE 5

The following compounds were prepared following essentially the same procedure as that described in Example 4 for the preparation of ethyl 2-{4-[N-(1,7-dichloroisoquinolin-3-yl)-N-methylamino]phenoxy}propionate (23):

(a) ethyl 2-{4-[N-(1-chloroisoquinolin-3-yl)-N-methylamino]phenoxy}propionate (25), oil;
(b) ethyl 2-{4-[N-(1-chloroisoquinolin-3-yl)amino]phenoxy}propionate (31), oil;
(c) ethyl 2-{4-[N-(7-bromo-1-chloroisoquinolin-3-yl)-N-methylamino]phenoxy}propionate (42), oil;
(d) ethyl 2-{4-[N-(1,6-dichloroisoquinolin-3-yl)-N-methyl]phenoxy}propionate (46), oil;
(e) ethyl 2-{4-[N-(1,7-dichloroisoquinolin-3-yl)amino]phenoxy}propionate (48), mp 105° C.;
(f) ethyl 2-{4-[N-(1-chloro-7-cyanoisoquinolin-3-yl)-N-methylamino]phenoxy}propionate (52), mp 134° C.;
(g) ethyl 2-{4-[N-(1,6,7-trichloroisoquinolin-3-yl)-N-methylamino]phenoxy}propionate (60), oil;
(h) ethyl 2-{4-[N-(1-chloro-6-fluoroisoquinolin-3-yl)-N-methylamino]phenoxy}propionate (63), oil;
(i) ethyl 2-{4-[N-(1,7-dichloro-6-fluoroisoquinolin-3-yl)-N-methylamino]phenoxy}propionate (67), oil;
(j) ethyl 2-{4-[N-(1,7-dichloroisoquinolin-3-yl)amino]-2-fluorophenoxy}propionate (68), oil;
(k) ethyl 2-{4-[N-(1,7-dichloro-6-cyanoisoquinolin-3-yl)-N-methylamino]phenoxy}propionate (69), oil; and
(l) methyl 2-{4-[N-(1,7-dichloroisoquinolin-3-yl)-N-methylamino]phenoxy}propionate (75), mp 85°–86° C.

The structure assigned to each compound was confirmed by proton magnetic resonance spectroscopy and mass spectrometry. Proton magnetic resonance spectra data is recorded in Example 39, Table 4.

EXAMPLE 6

Ethyl 2-{4-[N-(7-chloroisoquinolin-3-yl)-N-methylamino]phenoxy}propionate (24)

(a) Zinc powder (0.63 g) was added portionwise to a solution of 4-[N-(1,7-dichloroisoquinolin-3-yl)-N-methylamino]phenol (2.82 g) in a mixture of acetic acid (135 ml) and water (15 ml). On completion of the addition the mixture was heated under reflux for a period of 1 hour and was then filtered to remove any residual zinc. The solvent was removed by distillation under reduced pressure to give an oil. The oil was purified by chromatography over silica gel (eluant dichloromethane/ethyl acetate; 90:10) to give 4-[N-(7-chloroisoquinolin-3-yl)-N-methylamino]phenol (1.0 g) as an orange solid mp 140° C.

(b) A mixture of ethyl 2-bromopropionate (0.64 g), 4-[N-(7-chloroisoquinolin-3-yl)-N-methylamino]phenol (0.92 g), anhydrous potassium carbonate (0.49 g) and methyl ethyl ketone was heated under reflux for a period of 5 hours. The solution was cooled, washed with water, and dried over anhydrous magnesium sulfate. The solvent was removed by distillation under reduced pressure and the product was purified by column chromatography over silica gel (eluant dichloromethane) to give ethyl 2-{4-[N-(7-chloroisoquinolin-3-yl)-N-methylamino]phenoxy}propionate (1.00 g) as a green oil. The assigned structure was confirmed by proton magnetic resonance spectroscopy and mass spectrometry. Proton magnetic resonance spectrum (CDCl$_3$; δ in ppm): 1.25 (3H, t); 1.60 (3H, d); 3.45 (3H, s); 4.22 (2H, q); 4.75 (1H, q); 6.52 (1H, s); 6.8–7.4 (6H, m); 7.62 (1H, m); 8.75 (1H, s).

EXAMPLE 7

Ethyl 2-{4-[N-(isoquinolin-3-yl)-N-methylamino]phenoxy}propionate (26)

Ethyl 2-{4-[N-(1-chloroisoquinolin-3-yl)-N-methylamino]phenoxy}propionate (2.87 g), in a solution of potassium hydroxide (0.42 g) in ethanol, was hydrogenated at atmospheric pressure over a palladium on carbon catalyst. After uptake of the theoretical amount of hydrogen the solution was filtered to remove the catalyst and the solvent was removed by distillation under reduced pressure. The product was purified by column chromatography over silical gel (eluant dichloromethane/ethylacetate; 99:1) to give ethyl 2-{4-[N-(isoquinolin-3-yl)-N-methylamino]phenoxy}propionate (0.38 g) as a green oil. The assigned structure was confirmed by proton magnetic resonance spectroscopy and mass spectrometry. Proton magnetic resonance spectrum (CDCl$_3$; δ in ppm): 1.20 (3H, t); 1.60 (3H, d); 3.45 (3H, s); 4.20 (2H, q); 4.70 (1H, q); 6.60 (1H, s); 6.8–7.4 (7H, m); 7.65 (1H, d); 8.90 (1H, s).

EXAMPLE 8

Ethyl 2-{4-[(2-oxide-isoquinolin-3-yl)oxy]phenoxy}propionate (27)

(a) A mixture of 1,3-dichloroisoquinoline (26.0 g; prepared according to the method of G Simchen, *Angew. Chem. Internat. Ed.* 5 (7), 663, 1966), acetic acid (125 ml), hydrogen iodide (55 ml) and red phosphorus (9.0 g) was heated with stirring at a temperature of 170° C. for a period of 3 hours. After cooling the mixture was poured into ice-water and the aqueous mixture was neutralized with aqueous sodium hydroxide. The aqueous mixture was extracted with dichloromethane and the organic extract was dried over anhydrous magnesium sulfate. The solvent was evaporated to give an oil which was purified by column chromatography over silica gel (eluant dichloromethane) to give 3-chloroisoquinoline (18.23 g) mp<50° C.

A mixture of 3-chloroisoquinoline (18.23 g), m-chloroperbenzoic acid (36.46 g) and benzene (180 ml) was stirred at ambient temperature for a period of 2.5 days. The mixture was diluted with dichloromethane and the resultant solution was washed several times with a aqueous 5% sodium bicarbonate solution and finally with water. The organic phase was dried over anhydrous magnesium sulfate and the solvent was evaporated to give a solid residue. The solid was recrystallised from ethyl acetate to give 3-chloroisoquinoline-2-oxide (6.53 g) as colourless crystals mp 147°–151° C.

(b) A mixture of 3-chloroisoquinoline-2-oxide (1.0 g), ethyl 2-[4-hydroxyphenoxy]propionate, anhydrous potassium carbonate (0.91 g), copper powder (0.20 g) and dimethyl formamide was heated under reflux with stirring for a period of 7 hours. The mixture was cooled, filtered and the solvent was removed by distillation under reduced pressure to give an oil. The product was purified by column chromatography over silica gel (eluant ethyl acetate) to give ethyl 2-{4-[(2-oxide-isoquinolin-3-yl)oxy]phenoxy}propionate (0.39 g) as a brown oil. The assigned structure was confirmed by proton magnetic resonance spectroscopy and mass spectrometry. Proton magnetic resonance spectrum (CDCl$_3$; δ in ppm): 1.25 (3H, t); 1.60 (3H, d); 4.20 (2H, q); 4.68 (1H, q); 6.65–7.25 (5H, m); 7.25–7.75 (4H, m); 8.40 (1H, s).

EXAMPLE 9

Ethyl 2-{4-[(7-chloro-2-oxideisoquinolin-3-yl)oxy]phenoxy}propionate (32), solid mp <50° C., was prepared from 3,7-dichloroisoquinoline following essentially the same procedure as that described in Example 8.

The assigned structure was confirmed by proton magnetic resonance spectroscopy and mass spectrometry. Proton magnetic resonance spectrum (CDCl$_3$; δ in ppm): 1.27 (3H, t); 1.64 (3H, d); 4.25 (2H, q); 4.75 (1H, q); 6.70–7.30 (5H, m); 7.30–7.90 (3H, m); 8.35 (1H, s).

EXAMPLE 10

Ethyl 2-{4-[(isoquinolin-3-yl)oxy]phenoxy}propionate (28)

An aqueous solution of titanium trichloride (26.0 ml of a 15% solution) was added dropwise to a stirred solution of ethyl 2-{4-[(2-oxide-isoquinolin-3-yl)oxy]phenoxy}propionate (1.50 g) in acetone. On completion of the addition the solution was stirred for a further 20 minutes and then extracted with ethyl acetate. The organic phase was washed with water and dried over anhydrous magnesium sulfate. The solvent was removed by distillation under reduced pressure and the residue was purified by column chromatography over silica gel (eluant dichloromethane/ethyl acetate; 99:1) to give ethyl 2-{4-[(isoquinolin-3-yl)oxy]phenoxy}propionate (0.80 g) as a brown oil. The assigned structure was confirmed by proton magnetic resonance spectroscopy and mass spectrometry. Proton magnetic resonance spectrum (CDCl$_3$; δ in ppm): 1.22 (3H, t); 1.60 (3H, d); 4.20 (2H, q); 4.70 (1H, q); 6.7–8.0 (9H, m); 8.93 (1H, s).

EXAMPLE 11

Ethyl 2-{4-[(1-chloroisoquinolin-3-yl)oxy]phenoxy}propionate (29)

A mixture of ethyl 2-{4-[(2-oxide-isoquinolin-3-yl)oxy]phenoxy}propionate (1.69 g) and phosphorus oxychloride was heated under reflux for a period of 10 minutes. The mixture was poured into aqueous ethanol and extracted with dichloromethane. The organic phase was washed with water, dried over anhydrous magnesium sulfate and the solvent was removed by distillation under reduced pressure. The residue was purified by column chromatography over silica gel (eluant dichloromethane) to give ethyl 2-{4-[(1-chloroisoquinolin-3-yl)oxy]phenoxy}propionate (0.65 g) as a brown oil. The assigned structure was confirmed by proton magnetic resonance spectroscopy and mass spectrometry. Proton magnetic resonance spectrum (CDCl$_3$; δ in ppm): 1.25 (3H, t); 1.60 (3H, d); 4.20 (2H, q); 4.70 (1H, q); 6.8–7.7 (8H, m); 8.0–8.3 (1H, m).

EXAMPLE 12

Ethyl 2-{4-[(1,7-dichloroisoquinolin-3-yl)oxy]phenoxy}propionate (37), mp 99° C., was prepared from ethyl 2-{4-[(7-chloro-2-oxideisoquinolin-3-yl)oxy]phenoxy}propionate following essentially the same procedure as that described in Example 11.

The assigned structure was confirmed by proton magnetic resonance spectroscopy and mass spectrometry. Proton magnetic resonance spectrum (CDCl$_3$; δ in ppm): 1.25 (3H, t); 1.60 (3H, d); 4.25 (2H, q); 4.75 (1H, q); 6.85 (1H, s); 7.05 (4H, m); 7.65 (2H, m); 8.15 (1H, s).

EXAMPLE 13

Ethyl 2-{4-[N-(3-chloroisoquinolin-1-yl)amino]phenoxy}propionate (30)

(a) A mixture of 1,3-dichloroisoquinoline (5.0 g; see Example 8) and p-anisidine (3.1 g) was heated at a temperature of 170° C. for a period of 2 hours. After cooling the product was purified by column chromatography over silica gel (eluant dichloromethane) to give 3-chloro-1-[N-(4-methoxyphenyl)amino]isoquinoline (1.32 g) mp 101° C.

A mixture of 3-chloro-1-[N-(4-methoxyphenyl)amino]isoquinoline (1.90 g), hydrogen bromide (10 ml of 48%) and glacial acetic acid was heated under reflux for a period of 9.5 hours. The reaction mixture was poured into water, and the aqueous mixture was extracted with ethyl acetate. The organic phase was dried over anhydrous magnesium sulfate and the solvent was removed by distillation under reduced pressure to give 4-[N-(3-chloroisoquinolin-1-yl)amino]phenol (1.84 g) as pale yellow crystals mp 170° C.

(b) A mixture of ethyl 2-bromopropionate (1.33 g), 4-[N-(3-chloroisoquinolin-1-yl)amino]phenol (1.80 g), anhydrous potassium carbonate (1.01 g) and dimethyl formamide was heated, with stirring, at a temperature of 100° C. for a period of 1 hour. The mixture was cooled and poured into dichloromethane and the resulting mixture was repeatedly washed with water. The organic phase was dried over anhydrous magnesium sulfate and the solvent was removed by distillation under reduced pressure. The residue was purified by chromatography over silica gel (eluant dichloromethane) to give ethyl 2-{4-[N-(3-chloroisoquinolin-1-yl)amino]phenoxy}propionate (1.74 g) as a yellow oil. The assigned structure was confirmed by proton magnetic resonance spectroscopy and mass spectrometry. Proton magnetic resonance spectrum (CDCl$_3$; δ ppm); 1.20 (3H, t); 1.50 (3H, d); 4.12 (2H, q); 4.60 (1H, q); 6.60–8.20 (10H, m).

EXAMPLE 14

Ethyl 2-{4-[N-(1-chloro-7-fluoroisoquinolin-3-yl)-N-methylamino]phenoxy}propionate (45)

(a) A mixture of 4-fluoroaniline (27.75 g), acetone (500 ml) and hydrobromic acid (80 ml, 48%) stirred at −5° C. was treated over 30 minutes with a solution of sodium nitrite (21.0 g) in water (50 ml). Methyl acrylate (215 g) and cuprous bromide (0.04 g) were added. The internal temperature was allowed to rise in a carefully controlled manner; at 15° C. the evolution of N$_2$ was vigorous. When the rate of N$_2$ evolution decreased, the mixture was stirred at 25° C. for 1 hr to complete the reaction. The mixture was evaporated, and the residue was partitioned between water and toluene to give crude methyl 2-bromo-3-(4-fluorophenyl)propionate.

Crude methyl 2-bromo-3-(4-fluorophenyl)propionate in acetic acid (330 ml) was stirred and treated with zinc dust (32.75 g) in portions over 30 minutes. The mixture was stirred for an additional 30 minutes and filtered, and the filter cake was washed with acetic acid. After the filtrate was evaporated the residue was partitioned between methylene chloride and water to give crude methyl 3-(4-fluorophenyl)propionate, which was refluxed with aqueous sodium hydroxide (400 ml, 10%) for 2 hrs, cooled, treated with decolorizing carbon, and filtered. The filtrate was acidified with 5 N HCl and filtered. The filter cake was washed extensively with water to give 3-(4-fluorophenyl)propionic acid (20.0 g) as colourless crystals, mp 90° C.

A mixture of 3-(4-fluorophenyl)propionic acid (20.0 g) and polyphosphoric acid (800 g) was stirred and heated at 100° C. for 2 hr. The mixture was then poured into an ice/water mixture (1 kg) and extracted with ethyl acetate. The organic phase was washed with water, dilute sodium bicarbonate solution and water again, then dried (MgSO$_4$) and evaporated to give 6-fluoro-1-indanone (17.0 g) as a crystalline solid, mp 54° C.

To a solution of 6-fluoro-1-indanone (1.65 g) in a mixture of 2-methoxy ethanol (25 ml) and concentrated hydrochloric acid (5.8 ml) was added, with stirring, n-butylnitrite (1.5 ml). After standing for 2 hrs at room temperature the crystalline slurry was poured into cold water (140 ml) and the colourless crystalline precipitate filtered, washed with cold water and air dried.

Recrystallization from aqueous methanol gave 6-fluoro-2-oximino-1-indanone (1.25 g) as colourless crystals, mp (decomp) 260° C.

Phosphorus pentachloride (2.20 g) was added portionwise to a stirred solution of 6-fluoro-2-oximino-1-indanone (1.76 g) in methylene chloride (50 ml), which had N$_2$ bubbling through it. Nitrogen was continually bubbled through the solution for 2 hrs, then the mixture was filtered, evaporated to dryness and acetone and water were added. The mixture was stirred at room temperature for 3 hrs, then concentrated and diluted with water. The colourless precipitate was collected, washed with water to give 4-fluoro-2-carboxy phenylacetonitrile (1.17 g), mp 140° C.

A mixture of 4-fluoro-2-carboxyphenylacetonitrile (2.07 g), N-methyl-4-hydroxyaniline (2.8 g) and chlorobenzene (50 ml) was heated under reflux for a period of 2 hrs. The mixture was cooled and the product which crystallised was collected by filtration to give 4-[N-(7-fluoro-1-hydroxyisoquinolin-3-yl)-N-methylamino]phenol (2.08 g), mp 249° C.

A mixture of 4-[N-(7-fluoro-1-hydroxyisoquinolin-3-yl)-N-methylamino]phenol (2.08 g) and phosphorus oxychloride was heated under reflux for approximately 10 minutes at which stage a clear solution had been obtained. The mixture was cooled and poured into ice-water. The precipitated solid was collected and purified by column chromatography over silica gel (eluant dichloromethane/ethyl acetate; 90:10) to give 4-[N-(1-chloro-7-fluoroisoquinolin-3-yl)-N-methylamino]phenol (2.00 g) as a yellow crystalline solid mp 130° C.

(b) A mixture of ethyl 2-bromopropionate (1.12 g), 4-[N-(1-chloro-7-fluoroisoquinolin-3-yl)-N-methylamino]phenol (1.70 g), anhydrous potassium carbonate (0.86 g) and methyl ethyl ketone (20 ml) was heated under reflux for a period of 3 hours. The mixture was cooled, diluted with dichloromethane, washed with water and dried over anhydrous magnesium sulfate. The solvent was removed by distillation under reduced pressure to give an oil which was purified by column chromatography over silica gel (eluant dichloromethane) to give ethyl 2-{4-[N-(1-chloro-7-fluoroisoquinolin-3-yl)-N-methylamino]phenoxy}propionate (2.00 g) as a yellow oil. The assigned structure was confirmed by proton magnetic spectroscopy and mass spectrometry. Proton magnetic resonance spectrum (CDCl$_3$; δ in ppm): 1.29 (3H, t); 1.65 (3H, d); 3.47 (3H, s); 4.27 (2H, q); 4.75 (1H, q); 6.47 (1H, s) 6.85–7.20 (6H, m); 7.30 (1H, d).

EXAMPLE 15

The following compounds were prepared following essentially the same procedure as that described in Example 14 for the preparation of ethyl 2-{4-[N-(1-chloro-7-fluoroisoquinolin-3-yl)-N-methylamino]phenoxy}-propionate (45):

(a) ethyl 2-{4-[N-(1-chloro-7-methylisoquinolin-3-yl)-N-methylamino]phenoxy}propionate (41), oil;

(b) ethyl 2-{4-[N-(1-chloro-7-methoxyisoquinolin-3-yl)-N-methylamino]phenoxy}propionate (70), oil; and (c) methyl 2-{4-[N-(1-chloro-7-fluoroisoquinolin-3-yl)-N-methylamino]phenoxy}propionate (71), oil.

The structure assigned to each compound was confirmed by proton magnetic resonance spectroscopy and mass spectrometry. Proton magnetic resonance spectra data is recorded in Example 39, Table 4.

EXAMPLE 16

Ethyl 2-{4-[N-(7-fluoroisoquinolin-3-yl)-N-methylamino]phenoxy}propionate (72)

Zinc powder (4×1.63 g) was added portionwise over a 2 hr period to a stirred solution of ethyl 2-{4-[N-(1-chloro-7-fluoroisoquinolin-3-yl)-N-methylamino]phenoxy}propionate (1.00 g) in acetic acid (50 ml). The mixture was filtered and the filter cake was washed with acetic acid. After the filtrate was evaporated the residue was partitioned between methylene chloride and water. The organic extract was washed successively with, aqueous sodium bicarbonate solution, water, aqueous ethylenediaminetetraacetic acid solution (5%) and water, then dried (MgSO$_4$) and evaporated to give a green oil. Purification by column chromatography over silica gel (eluant dichloromethane) gave ethyl 2-[4-[N-(7-fluoroisoquinolin-3-yl)-N-methylamino]phenoxy}propionate (0.55 g) as a greenish oil. The assigned structure was confirmed by proton magnetic spectroscopy and mass spectrometry. Proton magnetic resonance spectrum (CDCl$_3$; δ in ppm): 1.28 (3H, t); 1.64 (3H, d); 3.48 (3H, s); 4.25 (2H, q); 4.74 (1H, q); 6.62 (1H; s); 6.87–7.37 (7H, m); 8.85 (1H, s).

EXAMPLE 17

The following compounds were prepared from the corresponding 1-chloro substituted compound following essentially the same procedure as that described in Example 16 for the preparation of ethyl 2-{4-[N-(7-fluoroisoquinolin-3-yl)-N-methylamino]phenoxy}propionate (72):

(a) ethyl 2-{4-[N-(4-chloroisoquinolin-3-yl)-N-methylamino]phenoxy}propionate (36), oil;
(b) ethyl 2-{4-[N-(4,7-dichloroisoquinolin-3-yl)-N-methylamino]phenoxy}propionate (40), oil; and
(c) ethyl 2-{4-[N-(6-chloroisoquinolin-3-yl)-N-methylamino]phenoxy}propionate (47), oil.

The structure assigned to each compound was confirmed by proton magnetic resonance spectroscopy and mass spectrometry. Proton magnetic resonance spectra data is recorded in Example 39, Table 4.

EXAMPLE 18

2-{4-[N-(1,7-Dichloroisoquinolin-3-yl)-N-methylamino]phenoxy}propionic acid (50)

A slight excess of ethanolic potassium hydroxide was added to a solution of ethyl 2-{4-[N-(1,7-dichloroisoquinolin-3-yl)-N-methylamino]phenoxy}propionate in ethanol at room temperature. The mixture was stirred for 12 hrs, then evaporated. The residue was diluted with water, acidified with dilute hydrochloric acid and extracted with dichloromethane. The dichloromethane extract was dried over sodium sulfate and then evaporated to give 2-{4-[N-(1,7-dichloroisoquinolin-3-yl)-N-methylamino]phenoxy}propionic acid as a yellow solid, mp 136° C.

EXAMPLE 19

2-{4-[N-(1,7-Dichloroisoquinolin-3-yl)-N-methylamino]phenoxy}propionic acid acetone oxime (55)

2-{4-[N-(1,7-Dichloroisoquinolin-3-yl)-N-methylamino]phenoxy}propionyl chloride was prepared by adding phosphorus pentachloride (1.07 g) portionwise to a solution of 2-{4-[N-(1,7-dichloroisoquinolin-3-yl)-N-methylamino]phenoxy}propionic acid (2.0 g) in dichloromethane at room temperature and stirring the reaction mixture for a period of 12 hours.

A solution of acetone oxime (0.41 g) in dichloromethane was added to the solution of the acid chloride in dichloromethane and the reaction mixture was stirred at room temperature for a period of 45 minutes. The solution was concentrated and the product was purified by chromatography over silica gel (eluant dichloromethane) to give 2-{4-[N-(1,7-dichloroisoquinolin-3-yl)-N-methylamino]phenoxy}propionic acid acetone oxime (0.70 g) as a yellow oil.

The assigned structure was confirmed by proton magnetic resonance spectroscopy and mass spectrometry. Proton magnetic resonance spectrum (CDCl$_3$; δ in ppm): 1.70 (3H, d); 1.90 (3H, s); 2.00 (3H, s); 3.40 (3H, s); 4.85 (1H, q); 6.33 (1H, s); 6.70–7.30 (6H, m); 7.90 (1H, s).

EXAMPLE 20

The following compounds were prepared from the appropriate acid chloride and the appropriate alcohol, thiol or amine following essentially the same procedure as that described in Example 19 for the preparation of 2-{4-[N-(1,7-dichloroisoquinolin-3-yl)-N-methylamino]phenoxy}propionic acid acetone oxime (55).

(a) 2-(N,N-dimethylamino)ethyl 2-{4-[N-(1,7-dichloroisoquinolin-3-yl)-N-methylamino]phenoxy}propionate (51), oil;
(b) 2-(N,N-dimethylamino)ethyl 2- 4-[N-(1,4,7-trichloroisoquinolin-3-yl)-N-methylamino]phenoxypropionate (53), oil;
(c) S-n-butyl 2-{4-[N-(1,7-dichloroisoquinolin-3-yl)-N-methylamino]phenoxy}propanethioate (56), oil; and
(d) N,N-di(n-propyl) 2-{4-[N-(1,7-dichloroisoquinolin-3-yl)-N-methylamino]phenoxy}propionamide (58), mp 113° C.

The structure assigned to each compound was confirmed by proton magnetic resonance spectroscopy and mass spectrometry. Proton magnetic resonance spectra data is recorded in Example 39, Table 4.

EXAMPLE 21

Ethyl 2-{4-[N-(1,4-dichloroisoquinolin-3-yl)-N-methylamino]phenoxy}propionate (33)

A mixture of ethyl 2-bromopropionate (1.36 g), 4-[N-(1-hydroxyisoquinolin-3-yl)-N-methylamino]phenol (2.00 g), anhydrous potassium carbonate (1.04 g) and methyl ethyl ketone (20 ml) was heated under reflux for a period of 3 hours. The mixture was cooled, washed with water and dried over anhydrous magnesium sulfate. The solvent was removed by distillation under reduced pressure to give an oil, which was purified by column chromatography over silica gel (eluant dichloromethane to yield ethyl 2-{4-[N-(1-hydroxyisoquinolin-3-yl)-N-methylamino]phenoxy}propionate (1.92 g) as a brown solid mp 96° C.

A mixture of ethyl 2-{4-[N-(1-hydroxyisoquinolin-3-yl)-N-methylamino]phenoxy}propionate (1.23 g), hydrogen peroxide (0.38 g, 30%), and concentrated hydrochloric acid (0.34 g) was stirred at room temperature for 90 mins and then poured into water. The aqueous mixture was extracted with dichloromethane which was then dried (MgSO$_4$) and evaporated to give a brown oil. Purification by column chromatography over silica gel (eluant dichloromethane) gave ethyl 2-{4-[N-4-chloro-1-hydroxyisoquinolin-3-yl)-N-methylamino]phenoxy}propionate (0.58 g) as a brown solid, mp 136° C.

A mixture of ethyl 2-{4-[N-(4-chloro-1-hydroxyisoquinolin-3-yl)-N-methylamino]phenoxy}propionate (2.23 g) and phosphorus oxychloride was heated under reflux for approximately 5 minutes at which stage a clear solution had been obtained. The mixture was cooled and poured into ice-water. This was extracted with dichloromethane, dried (MgSO$_4$) and evaporated to give a crude oil, which was purified by column chromatography over silica gel (eluant dichloromethane) to yield ethyl 2-{4-[N-(1,4-dichloroisoquinolin-2-yl)-N-methylamino]phenoxy}propionate (0.74 g) as a yellow oil.

The assigned structure was confirmed by proton magnetic resonance spectroscopy and mass spectrometry. Proton magnetic resonance spectrum (CDCl$_3$ δ in ppm): 1.20 (3H, t); 1.55 (3H, d); 3.40 (3H, s); 4.15 (2H, q); 4.55 (1H, q); 6.68 (4H, s); 7.10–8.20 (4H, m).

EXAMPLE 22

Ethyl 2-{4-[N-(1,4,7-trichloroisoquinolin-3-yl)-N-methylamino]phenoxy}propionate (35), an oil, was prepared from 4-[N-(7-chloro-1-hydroxyisoquinolin-3-yl)-N-methylamino]phenol following essentially the same procedure as that described in Example 21 above.

The assigned structure was confirmed by proton magnetic resonance spectroscopy and mass spectrometry. Proton magnetic resonance spectrum (CDCl$_3$; δ in ppm): 1.15 (3H, t); 1.60 (3H, d); 3.50 (3H, s); 4.20 (2H, q); 4.70 (1H, q); 6.80 (4H, m); 7.15–8.25 (3H, m).

EXAMPLE 23

Ethyl 2-{4-[N-(1-bromo-7-chloroisoquinolin-3-yl)-N-methylamino]phenoxy}propionate (39)

A mixture of ethyl 2-{4-[N-(7-chloro-1-hydroxyisoquinolin-3-yl)-N-methylamino]phenoxy}propionate (1.00 g) and phosphorus oxybromide was heated at 120° C. for 10 mins. The mixture was cooled, poured into ice-water and extracted with dichloromethane, which was dried (MgSO$_4$) and evaporated to give an oil. Purification by column chromatography over silica gel (eluant dichloromethane) gave ethyl 2-{4-[N-(1-bromo-7-chloroisoquinolin-3-yl)-N-methylamino]phenoxy}propionate (0.83 g) as a yellow oil.

The assigned structure was confirmed by proton magnetic resonance spectroscopy and mass spectrometry. Proton magnetic resonance spectrum (CDCl$_3$; δ in ppm): 1.25 (3H, t); 1.65 (3H, d); 3.50 (3H, s); 4.30 (2H, q); 4.80 (1H, q); 6.42 (1H, s); 7.10 (4H, m); 7.28 (2H, m); 8.00 (1H, s).

EXAMPLE 24

Ethyl 2-{4-[N-(1-bromoisoquinolin-3-yl)-N-methylamino]phenoxy}propionate (38), an oil, was prepared from ethyl 2-{4-[N-(1-hydroxyisoquinolin-3-yl)-N-methylamino]phenoxy}propionate following essentially the same procedure as that described in Example 23 above.

The assigned structure was confirmed by proton magnetic resonance spectroscopy and mass spectrometry. Proton magnetic resonance spectrum (CDCl$_3$; δ in ppm): 1.30 (3H, t); 1.65 (3H, d); 3.50 (3H, s); 4.25 (2H, q); 4.75 (1H, q); 6.45 (1H, s); 6.80–7.50 (7H, m); 8.00 (1H, m).

EXAMPLE 25

Methyl 2-{4-[N-(7-chloro-1-methoxyisoquinolin-3-yl)-N-methylamino]phenoxy}propionate (44)

(i) A mixture of ethyl 2-{4-[N-(1,7-dichloroisoquinolin-3-yl)-N-methylamino]phenoxy}propionate (1.25 g), sodium methoxide (0.63 g) and toluene was heated under reflux for 4 hrs. The mixture was cooled, poured into water and extracted with ethyl acetate. The organic fraction was dried (MgSO$_4$) and evaporated to give 2-{4-[N-(7-chloro-1-methoxyisoquinolin-3-yl)-N-methylamino]phenoxy}propionic acid.

(ii) the above acid was dissolved in methanol containing several drops of concentrated sulfuric acid. The mixture was refluxed for 1 hr, cooled, concentrated, dissolved in dichloromethane, washed repeatedly with water, dried (MgSO$_4$) and evaporated. Purification by column chromatography over silica gel (eluant dichloromethane) gave methyl 2-{4-[N-(7-chloro-1-methoxyisoquinolin-3-yl)-N-methylamino]phenoxy}propionate (0.44 g) as a yellow oil.

The assigned structure was confirmed by proton magnetic resonance spectroscopy and mass spectrometry. Proton magnetic resonance spectrum (CDCl$_3$; δ in ppm): 1.60 (3H, d); 3.42 (3H, s); 3.75 (3H, s); 3.97 (3H, s); 4.75 (1H, q); 6.75–7.30 (7H, m); 7.92 (1H, m).

EXAMPLE 26

2-{4-[N-(1-Methoxyisoquinolin-3-yl)-N-methylamino]phenoxy}propionic acid (43), mp 50° C., was prepared following essentially the same procedure as that described in Example 25 part (i).

The assigned structure was confirmed by proton magnetic resonance spectroscopy and mass spectrometry. Proton magnetic resonance spectrum (CDCl$_3$; δ in ppm): 1.65 (3H, d); 3.42 (3H, s); 2.97 (3H, s); 4.75 (1H, q); 6.15 (1H, s); 6.80–7.50 (9H, m); 8.00 (1H, m).

EXAMPLE 27

Ethyl 2-{4-[N-(1,7-dichloroisoquinolin-3-yl)-N-ethylamino]phenoxy}propionate (49)

A mixture of ethyl 2-{4-[N-(1,7-dichloroisoquinolin-3-yl)amino]phenoxy}propionate (0.36 g), sodium hydride (0.05 g, 60%) and dimethylformamide (10 ml) was stirred at room temperature for 15 minutes. Ethyl iodide (0.17 g) was added and stirring was continued for a further 15 minutes. The mixture was then poured into ethyl acetate and washed with water, dried (MgSO$_4$) and evaporated. Purification by column chromatography over silica gel gave ethyl 2-{4-[N-(1,7-dichloroisoquinolin-3-yl)-N-ethylamino]phenoxy}propionate as a yellow oil (0.40 g).

The assigned structure was confirmed by proton magnetic resonance spectroscopy and mass spectrometry. Proton magnetic resonance spectrum (CDCl$_3$; δ in ppm): 1.25 (6H, t); 1.60 (3H, d); 3.95 (2H, q); 4.25 (2H, q); 4.75 (1H, q); 6.20 (1H, s); 7.00–7.80 (6H, m); 7.95 (1H, s).

EXAMPLE 28

2-(Dimethylamino)ethyl
2-{4-[N-(1,7-dichloroisoquinolin-3-yl)-N-methylamino]phenoxy}propionate methyl iodide salt (57)

A solution of 2-(dimethylamino)ethyl 2-{4-[N-(1,7-dichloroisoquinolin-3-yl)-N-methylamino]phenoxy}-propionate in dichloromethane was added to a large excess of methyl iodide in dichloromethane. The mixture was stirred for 2 hrs at room temperature, then evaporated to give 2-dimethyl amino)ethyl 2-{4-[N-(1,7-dichloroisoquinolin-3-yl)-N-methylamino]phenoxy}propionate methyl iodide salt as yellow crystals mp 76° C.

EXAMPLE 29

Ethyl
2-{4-[N-(1-cyanoisoquinolin-3-yl)-N-methylamino]phenoxy}propionate (59)

A mixture of ethyl 2-{4-[N-(1-chloroisoquinolin-3-yl)-N-methylamino]phenoxy}propionate (1.00 g), cuprous cyanide (5.0 g) and dry dimethyl sulfoxide (10 ml) was stirred at 120° C. for 48 hours. The cooled mixture was dissolved in methylene chloride and washed repeatedly with water, then dried (MgSO$_4$) and evaporated. Purification by column chromatography over silica gel (eluant; methyl chloride) gave ethyl 2-{4-[N-(1-cyanoisoquinolin-3-yl)-N-methylamino]phenoxy}propionate (0.30 g) as a brown oil.

The assigned structure was confirmed by proton magnetic resonance spectroscopy and mass spectrometry. Proton magnetic resonance spectrum (CDCl$_3$; δ in ppm): 1.30 (3H, t); 1.67 (3H, d); 3.50 (3H, s); 4.27 (2H, q); 4.78 (1H, q); 6.78 (1H, s); 6.90–7.40 (7H, m); 8.02 (1H, d).

EXAMPLE 30

Ethyl 2-{4-[N-(7-chloro-1-cyanoisoquinolin-3-yl)-N-methylamino]phenoxy}propionate (61) was prepared from ethyl 2-{4-[N-(1,7-dichloroisoquinolin-3-yl)-N-methylamino]phenoxy}propionate following essentially the same procedure as that described in Example 29.

The assigned structure was confirmed by proton magnetic resonance spectroscopy and mass spectrometry. Proton magnetic resonance spectrum (CDCl$_3$; δ in ppm): 1.31 (3H, t); 1.67 (3H, d); 3.49 (3H, s); 4.27 (2H, q); 4.78 (1H, q); 6.73 (1H, s); 7.10 (4H, q); 7.33 (2H, s); 7.29 (1H, s).

EXAMPLE 31

Ethyl
2-{4-[N-(7-chloro-1-fluoroisoquinolin-3-yl)-N-methylamino]phenoxy}propionate (66) and ethyl 2-{4-[N-(7-chloro-1-methylthioisoquinolin-3-yl)-N-methylamino]phenoxy}propionate (65)

A mixture of ethyl 2-{4-[N-(1,7-dichloroisoquinolin-3-yl)-N-methylamino]phenoxy}propionate (0.90 g), anhydrous potassium fluoride (1.50 g) and dry dimethyl sulfoxide (10 ml) was stirred at 160° C. for 48 hrs. The cooled mixture was dissolved in methylene chloride and washed repeatedly with water, then dried (MgSO$_4$) and evaporated to give a crude, brown oil. Purification by column chromatography over silica gel (eluant: methylene chloride/hexane) gave Ethyl 2-{4-[N-(7-chloro-1-methylthioisoquinolin-3-yl)-N-methylamino]phenoxy}-propionate (0.060 g) as a yellow oil and ethyl 2-{4-[N-(7-chloro-1-fluoroisoquinolin-3-yl)-N-methylamino]phenoxy}propionate (0.180 g) as a yellow oil.

The structure assigned to each compound was confirmed by proton magnetic resonance spectroscopy and mass spectrometry. Proton magnetic resonance spectrum of the 1-methylthio substituted product (compound no 65) (CDCl$_3$; δ in ppm): 1.28 (3H, t); 1.65 (3H, d); 2.59 (3H, s); 3.51 (3H, s); 4.25 (2H, q); 4.76 (1H, q); 6.23 (1H, s); 6.85–7.35 (6H, m); 7.91 (1H, s). Proton magnetic resonance spectrum of the 1-fluoro substituted product (compound no 66 (CDCl$_3$; δ in ppm): 1.29 (3H, t); 1.65 (3H, d); 3.43 (3H, s); 4.26 (2H, q); 4.76 (1H, q); 6.30 (1H, s); 6.85–7.35 (6H, m); 7.84 (1H, s).

EXAMPLE 32

Ethyl 2-{4-[N-(1,7-difluoroisoquinolin-3-yl)-N-methylamino]phenoxy}propionate (62) was prepared from ethyl 2-{4-[N-(1-chloro-7-fluoroisoquinolin-3-yl)-N-methylamino]phenoxy propionate following essentially the same procedure as that described in Example 31.

The assigned structure was confirmed by proton magnetic resonance spectroscopy and mass spectrometry. Proton magnetic resonance spectrum (CDCl$_3$; δ in ppm): 1.29 (3H, t); 1.65 (3H, d); 3.43 (3H, s); 4.26 (2H, q); 4.76 (1H, q); 6.37 (1H, s); 6.85–7.60 (7H, m).

EXAMPLE 33 n-Propyl
2-{4-[N-(1,7-dichloroisoquinolin-3-yl)-N-methylamino]phenoxy}propionate (73)

A mixture of ethyl 2-{4-[N-(1,7-dichloroisoquinolin-3-yl)-N-methylamino]phenoxy}propionate (1.04 g), n-propanol and a trace of concentrated sulfuric acid was heated under reflux for 4 hours. The mixture was concentrated and then partitioned between dichloromethane and water. The dichloromethane layer was washed with water, dried over MgSO$_4$ and evaporated to give n-propyl 2-{4-[N-(1,7-dichloroisoquinolin-3-yl)-N-methylamino]phenoxy}propionate (0.72 g) as a yellow oil.

The assigned structure was confirmed by proton magnetic resonance spectroscopy and mass spectrometry. Proton magnetic resonance spectrum (CDCl$_3$; δ in ppm): 0.90 (3H, t); 1.65 (5H, m); 3.40 (3H, s); 4.10 (2H, t); 4.70 (1H, q); 6.30 (1H, s); 6.70–7.40 (6H, m); 7.90 (1H, s).

EXAMPLE 34 n-Butyl 2-{4-N-(1,7-dichloroisoquinolin-3-yl)-N-methylamino]phenoxy}propionate (74) was prepared by transesterification following essentially the same procedure as that described in Example 33.

The assigned structure was confirmed by proton magnetic resonance spectroscopy and mass spectrometry. Proton magnetic resonance spectrum (CDCl$_3$; δ in ppm): 0.70–1.90 (10H, m); 3.45 (3H, s); 4.20 (2H, t); 4.75 (1H, q); 6.30 (1H, s); 6.70–7.40 (6H, m); 7.90 (1H, s).

EXAMPLE 35

Ethyl
2-{4-[N-(1,7-dichloroisoquinolin-3-yl)-N-methylamino]phenoxy}acetate (77)

A mixture of ethyl 2-bromoacetate (0.23 g), 4-[N-(1,7-dichloroisoquinolin-3-yl)-N-methylamino]phenol (0.40 g), anhydrous potassium carbonate (0.19 g) and methyl ethyl ketone was heated under reflux for 12 hrs. The mixture was cooled, diluted with dichloromethane, washed with water and dried over anhydrous magnesium sulfate. The solvent was evaporated to give an oil, which was purified by column chromatography over silica gel (eluant dichloromethane) to give ethyl 2-{4-[N-(1,7-dichloroisoquinolin-3-yl)-N-methylamino]-phenoxy}acetate (0.52 g) as a yellow crystalline solid, mp 99° C.

The assigned structure was confirmed by proton magnetic resonance spectroscopy and mass spectrometry.

EXAMPLE 36

Ethyl 2-methyl-2-{4-[N-(1,7-dichloroisoquinolin-3-yl)-N-methylamino]phenoxy}propionate (78)

A mixture of ethyl 2-bromo-2-methylpropionate (0.54 g), 4-[N-(1,7-dichloroisoquinolin-3-yl)-N-methylamino]phenol (0.74 g), potassium carbonate (0.38 g) dimethylformamide was heated at 100° C. for 28 hrs. The mixture was cooled, diluted with dichloromethane, washed with water and then dried over anhydrous magnesium sulfate. The solvent was evaporated to give an oil, which was purified by column chromatography over silica gel (eluent dichloromethane) to give ethyl 2-methyl-2-{4-[N-(1,7-dichloroisoquinolin-3-yl)-N-methylamino]-phenoxy}propionate (0.55 g) as a yellow oil.

The assigned structure was confirmed by proton magnetic resonance spectroscopy and mass spectrometry. Proton magnetic resonance spectrum (CDCl$_3$; δ in ppm): 1.50 (3H, t); 1.65 (6H, s); 3.45 (3H, s); 4.30 (2H, q); 6.90 (1H, s); 7.10 (4H, q); 7.20 (2H, s); 8.00 (1H, s).

EXAMPLE 37

Ethyl 2-{4-[7-chloroisoquinolin-3-yl)oxy]phenoxy}-propionate (34)

(a) A mixture of 3,7-dichloroisoquinoline (5.59 g), sodium 4-methoxyphenoxide (4.55 g), potassium carbonate (3.86 g) copper powder (50 mg) and trace of copper oxide were heated at 180° C. for 14 hrs. the mixture was then cooled and extracted with ethyl acetate, which in turn was washed with water, dried (MgSO$_4$) and evaporated to give a crude brown solid. Purification by column chromatography over silica gel gave 7-chloro-3-(4-methoxyphenoxy)isoquinoline (3.70 g) as a tan solid, mp 77° C.

(b) 7-Chloro-3-(4-methoxyphenoxy)isoquinoline (3.50 g) was refluxed in a mixture of acetic acid (25 ml) and a solution of hydrogen bromide (25 ml, 48%) for 3 hrs. The mixture was cooled, poured into water, neutralized with sodium carbonate and extracted with ethyl acetate. The extract was washed thoroughly with water, dried (MgSO$_4$) and evaporated to give 4-[(7-chloroisoquinolin-3-yl)oxy]phenol (3.02 g) as brown solid, mp 190° C.

(c) 4-[(7-chloroisoquinolin-3-yl)oxy]phenol (2.82 g) and ethyl 2-bromopropionate (2.07 g) in the presence of anhydrous potassium carbonate (1.58 g) were refluxed in methyl ethyl ketone (50 ml) for 4 hrs. The mixture was cooled, poured into dichloromethane, washed with water, dried (MgSO$_4$) and evaporated. Purification by column chromatography over silica gel (eluant dichloromethane) gave ethyl 2-{4-[(7-chloroisoquinolin-3-yl)oxy]phenoxy}propionate (3.33 g) as a brown oil.

The assigned structure was confirmed by proton magnetic resonance spectroscopy and mass spectrometry. Proton magnetic resonance spectrum (CDCl$_3$; δ in ppm): 1.15 (3H, t); 1.60 (3H, d); 4.25 (2H, q); 4.75 (1H, q); 6.80-7.90 (7H, m); 8.90 (1H, s).

EXAMPLE 38

Ethyl 2-{4-[(7-fluoroisoquinolin-3-yl)oxy]phenoxy}-propionate (64), an oil, was prepared from 3-chloro-7-fluoroisoquinoline following essentially the same procedure as that described in Example 37.

The assigned structure was confirmed by proton magnetic resonance spectroscopy and mass spectrometry. Proton magnetic resonance spectrum (CDCl$_3$; δ in ppm): 1.26 (3H, t); 1.62 (3H, d); 4.23 (2H, q); 4.74 (1H, q); 6.86-7.45 (8H, m); 8.88 (1H, s).

EXAMPLE 39

The majority of the compounds prepared as described in Examples 5, 15, 17 and 20 are oils and were characterised by, and can be identified by their proton magnetic resonance (pmr) spectrum. For convenience the pmr spectroscopic data is recorded in Table 4 below:

TABLE 4

| Compound No | Proton Chemical Shift in δ ppm (CDCl$_3$) |
|---|---|
| 25 | 1.15(3H,t); 1.5(3H,d); 3.35(3H,s); 4.15(2H,q); 4.65(1H,q); 6.32(1H,s); 6.70-7.40(6H,m); 7.85(1H,m); 7.95(1H,m). |
| 31 | 1.20(3H,t); 1.60(3H,d); 4.20(2H,q); 4.70(1H,q); 6.50-7.50(8H,m); 8.00(1H,m). |
| 36 | 1.25(3H,t); 1.65(3H,d); 3.50(3H,s); 4.30(2H,q); 4.75(1H,q); 6.90(4H,s); 7.50-8.40(4H,m); 9.15(1H,s). |
| 40 | 1.20(3H,t); 1.55(3H,d); 3.45(3H,s); 4.20(2H,q); 4.65(1H,q); 6.75(4H,s);6.95-8.15(3H,m); 8.80(1H,s). |
| 41 | 1.28(3H,t); 1.64(3H,d); 2.41(3H,s); 3.46(3H,s); 4.25(2H,q); 4.75(1H,q); 6.46(1H,s); 6.80-7.30(6H,m); 7.81(1H,s). |
| 42 | 1.3(3H,t); 1.7(3H,d); 3.5(3H,s); 4.3(2H,q); 4.8(2H,q); 6.4(1H,s); 6.9-7.5(6H,m); 8.1(1H,m). |
| 46 | 1.25(3H,t); 1.60(3H,d); 3.44(3H,s); 4.25(2H,q); 4.75(1H,q); 6.25(1H,s); 6.80-7.40(6H,m); 7.85(1H,d). |
| 47 | 1.30(3H,t); 1.65(3H,d); 3.50(3H,s); 4.25(2H,q); 4.75(1H,q); 6.50(1H,s); 6.80-7.50(6H,m); 7.67(1H,d); 8.83(1H,s). |
| 48 | 1.30(3H,t); 1.65(3H,d); 4.25(3H,q); 4.75(1H,q); 6.40-7.60(8H,m); 8.10(1H,s). |
| 51 | 1.6(3H,d); 2.2(6H,s); 2.5(2H,t); 3.4(3H,s); 4.3(2H,t); 4.8(1H,q); 6.3(1H,s); 6.8-7.3(6H,m); 7.9(1H,m). |
| 52 | 1.27(3H,t); 1.65(3H,d); 3.50(3H,s); 4.25(2H,q); 4.77(1H,q); 6.35(1H,s); 6.80-7.50(6H,m); 8.30(1H,s). |
| 53 | 1.6(3H,d); 2.2(6H,s); 2.5(2H,t); 3.4(3H,s); 4.3(2H,t); 4.8(1H,q); 6.7-8.2(7H,m). |
| 56 | 0.92(3H,d); 1.16-1.75(7H,m); 2.90(2H,t); 3.50(3H,s); 4.79(1H,q); 6.42(1H,s); 6.80-7.40(6H,m); 7.95(1H,s). |
| 60 | 1.29(3H,t); 1.66(3H,d); 3.48(3H,s); 4.27(2H,q); 4.77(1H,q); 6.27(1H,s); 7.06(4H,q); 7.45(1H,s); 8.13(1H,s). |
| 63 | 1.29(3H,t); 1.65(3H,d); 3.47(3H,s); 4.26(2H,q); 4.77(1H,q); 6.33(1H,s); 7.07(6H,m); 7.98(1H,m). |
| 67 | 1.29(3H,t); 1.65(3H,d); 3.47(3H,s); 4.26(2H,q); 4.77(1H,q); 6.30(1H,s); 7.02(5H,m); 8.09(1H,d). |
| 68 | 1.28(3H,t); 1.65(3H,d); 4.24(2H,q); 4.74(1H,q); 6.57(1H,s); 6.80-7.25(4H,m); 7.46(1H,d); 8.08(1H,d). |
| 69 | 1.30(3H,t); 1.65(3H,d); 3.49(3H,s); 4.27(2H,q); 4.78(1H,q); 6.37(1H,s); 7.08(4H,q); 7.73(1H,s); 8.11(1H,s). |

TABLE 4-continued

| Compound No | Proton Chemical Shift in δ ppm (CDCl₃) |
|---|---|
| 70 | 1.27(3H,t); 1.63(3H,d); 3.45(3H,s); 3.86(3H,s); 4.24(2H,q); 4.75(1H,q); 6.49(1H,s); 7.14(7H,m). |
| 71 | 1.64(3H,d); 3.45(3H,s); 3.79(3H,s); 4.78(1H,q); 6.45(1H,s); 6.87–7.66(7H,m). |

EXAMPLE 40

Concentrated formulations of the compounds of the invention were prepared by:

(a) in the case of oils and waxy solids, dissolving the compound in toluene containing 7% v/v "Teric" N13 ("Teric" is a Trade Mark and "Teric" N13, a product of ethoxylation of nonylphenol, is available from ICI Australia Limited) and 3% v/v "Kemmat" SC15B ("Kemmat" is a Trade Mark and "Kemmat" SC15B is a formulation of calcium dodecylbenzene sulfonate); or (b) in the case of crystalline solids, adding 5 parts by weight of the compound and 1 part by weight of "Dyapol" PT ("Dyapol" is Trade Mark and "Dyapol" PT is an anionic suspending agent) to 94 parts by weight of an aqueous solution containing 0.25% v/v of "Teric" N8 (a product of ethoxylation of nonylphenol) and ball-milling the mixture to produce a stable suspension. The emulsifiable concentrates and suspensions were then diluted with water to give an aqueous composition of the required concentration suitable for use in the evaluation of the pre-emergence and post-emergence herbicidal activity of the compounds of the invention.

EXAMPLE 41

The pre-emergent herbicidal activity of the compounds of the invention formulated as described in Example 40 was assessed by the following procedure.

The seeds of the test species were sown in rows 2 cm deep in soil contained in seed boxes. The monocotyledonous plants and the dicotyledonous plants were sown in separate boxes and after sowing the two boxes were sprayed with the required quantity of a composition of the invention. Two duplicate seed boxes were prepared in the same manner but were not sprayed with a composition of the invention and were used for comparison purposes. All the boxes were placed in a glasshouse, lightly watered with an overhead spray to initiate germination and then sub-irrigated as required for optimum plant growth. After three weeks the boxes were removed from the glasshouse and the effect of the treatment was visually assessed. The results are presented in Tables 5a and 5b. In Table 5a the damage to plants is rated on a scale of from 0 to 3 where 0 represents from 0 to 25% damage, 3 represents 75 to 99% kill and 3+ represents 100% kill. In Table 5b the damage to plants is rated on a scale of from 0 to 5 where 0 represents from 0 to 10% damage, 1 represents from 11 to 30% damage, 2 represents from 31 to 60% damage, 3 represents from 61 to 80% damage, 4 represents from 81 to 99% damage and 5 represents 100% kill. A dash (—) means that no experiment was carried out.

The names of the test plants were as follows:

| | |
|---|---|
| Wh | Wheat |
| Ot | Wild Oats |
| Rg | Ryegrass |
| Jm | Japanese millet |
| P | Peas |
| Ip | Ipomea |
| Ms | Mustard |
| Sf | Sunflower |

PRE-EMERGENCE HERBICIDAL ACTIVITY

TABLE 5a

| Compound No | Application Rate kg/ha | Wh | Ot | Rg | Jm | P | Ip | Ms | Sf |
|---|---|---|---|---|---|---|---|---|---|
| 23 | 5.0 | 0 | 3+ | 3+ | 3+ | 0 | 0 | 0 | 0 |
| 23 | 1.0 | 0 | 0 | 2 | 1 | 0 | 0 | 0 | 0 |
| 26 | 5.0 | 0 | 0 | 3 | 3 | 0 | 0 | 0 | 0 |
| 26 | 1.0 | 0 | 0 | 0 | 0 | 0 | 0 | 0 | 0 |
| 25 | 5.0 | 0 | 0 | 3 | 3 | 0 | 0 | 0 | 0 |
| 27 | 5.0 | 0 | 0 | 2 | 3 | 0 | 0 | 0 | 0 |
| 29 | 5.0 | 1 | 0 | 3+ | 3+ | 0 | 0 | 0 | 0 |
| 29 | 1.0 | 0 | 0 | 0 | 2 | 0 | 0 | 0 | 0 |
| 24 | 5.0 | 2 | 1 | 3 | 3+ | 0 | 0 | 0 | 0 |
| 24 | 1.0 | 0 | 0 | 3 | 3 | 0 | 0 | 0 | 0 |

TABLE 5b

| Compound No | Application Rate kg/ha | Wh | Ot | Rg | Jm | P | Ip | Ms | Sf |
|---|---|---|---|---|---|---|---|---|---|
| 32 | 5.0 | 4 | 1 | 4 | 4 | 0 | 0 | 0 | 0 |
| 32 | 1.0 | 0 | 0 | 0 | 0 | 0 | 0 | 0 | 0 |
| 34 | 5.0 | 4 | 5 | 5 | 5 | 0 | 0 | 0 | 0 |
| 34 | 1.0 | 4 | 1 | 4 | 4 | 0 | 0 | 0 | 0 |
| 34 | 0.5 | 0 | 0 | 4 | 4 | 0 | 0 | 0 | 0 |
| 34 | 0.25 | 0 | 0 | 0 | 0 | 0 | 0 | 0 | 0 |
| 35 | 5.0 | 0 | 0 | 0 | 0 | 0 | 0 | 0 | 0 |
| 35 | 1.0 | 0 | 0 | 0 | 0 | 0 | 0 | 0 | 0 |
| 37 | 5.0 | 2 | 1 | 3 | 5 | 0 | 0 | 0 | 0 |
| 37 | 1.0 | 0 | 0 | 0 | 1 | 0 | 0 | 0 | 0 |
| 39 | 5.0 | 0 | 0 | 4 | 4 | 0 | 0 | 0 | 0 |
| 39 | 1.0 | 0 | 0 | 0 | 0 | 0 | 0 | 0 | 0 |
| 40 | 0.5 | 0 | 0 | 0 | 0 | 0 | 0 | 0 | 0 |
| 41 | 5.0 | 0 | 0 | 4 | 5 | 0 | 0 | 0 | 0 |
| 41 | 1.0 | 0 | 0 | 0 | 0 | 0 | 0 | 0 | 0 |
| 42 | 5.0 | 0 | 0 | 4 | 4 | 0 | 0 | 0 | 0 |
| 42 | 1.0 | 0 | 0 | 0 | 0 | 0 | 0 | 0 | 0 |
| 45 | 5.0 | 0 | 1 | 5 | 5 | 0 | 0 | 0 | 0 |
| 45 | 1.0 | 0 | 0 | 3 | 4 | 0 | 0 | 0 | 0 |
| 45 | 0.5 | 0 | 0 | 3 | 0 | 0 | 0 | 0 | 0 |
| 45 | 0.25 | 0 | 0 | 2 | 0 | 0 | 0 | 0 | 0 |
| 61 | 5.0 | 0 | 4 | 5 | 5 | 0 | 0 | 0 | 0 |
| 61 | 1.0 | 0 | 0 | 3 | 5 | 0 | 0 | 0 | 0 |
| 78 | 5.0 | 0 | 0 | 5 | 5 | 0 | 0 | 0 | 0 |
| 78 | 1.0 | 0 | 0 | 0 | 0 | 0 | 0 | 0 | 0 |

EXAMPLE 42

The post-emergent herbicidal activity of the compounds of the invention formulated as described in Example 40 was assessed by the following procedure.

The seeds of the test species were sown in rows 2 cm deep in soil contained in seed boxes. The monocotyledonous plants and the dicotyledonous plants were sown in separate seed boxes in duplicate. The four seed boxes were placed in a glasshouse, lightly watered with an overhead spray to initiate germination and then sub-irrigated as required for optimum plant growth. After the plants had grown to a height of about 10 to 12.5 cm one box of each of the monocotyledonous plants and the dicotyledonous plants were removed from the glasshouse and sprayed with the required quantity of a composition of the invention. After spraying the boxes were returned to the glasshouse for a further 3 weeks and the effect of treatment was visually assessed by comparison with the untreated controls. The results are presented in Tables 6a and 6b. In Table 6a the damage to plants is rated on a scale from 0 to 3 where 0 represents 0 to 25% damage, 3 represents 75 to 99% kill and 3+ represents 100% kill. In table 6b the damage to plants is rated on a scale from 0 to 5 where 0 represents from 0 to 10% damage, 1 represents from 11 to 30% damage, 2 represents from 31 to 60% damage, 3 represents from 61 to 80% damage, 4 represents from 81 to 99% damage and 5 represents 100% kill. A dash (—) means that no experiment was carried out.

The names of the test plants were as follows:

| | |
|---|---|
| Wh | Wheat |
| Ot | Wild Oats |
| Rg | Ryegrass |
| Jm | Japanese millet |
| P | Peas |
| Ip | Ipomea |
| Ms | Mustard |
| Sf | Sunflower |

POST-EMERGENCE HERBICIDAL ACTIVITY

TABLE 6a

| Compound No | Application Rate kg/ha | Test Plant | | | | | | | |
|---|---|---|---|---|---|---|---|---|---|
| | | Wh | Ot | Rg | Jm | P | Ip | Ms | Sf |
| 23 | 5.0 | 1 | 3 | 3+ | 3+ | 0 | 0 | 0 | 0 |
| 23 | 1.0 | 0 | 3 | 3 | 3+ | 0 | 0 | 0 | 0 |
| 26 | 5.0 | 3 | 0 | 3+ | 3+ | 0 | 0 | 0 | 0 |
| 26 | 1.0 | 1 | 0 | 3 | 3+ | 0 | 0 | 0 | 0 |
| 25 | 5.0 | 0 | 0 | 2 | 3+ | 0 | 0 | 0 | 0 |
| 27 | 5.0 | 0 | 0 | 3 | 3+ | 0 | 0 | 0 | 0 |
| 29 | 5.0 | 3 | 1 | 3+ | 3+ | 0 | 0 | 0 | 0 |
| 29 | 1.0 | 3 | 0 | 3 | 3+ | 0 | 0 | 0 | 0 |
| 24 | 5.0 | 3+ | 3+ | 3+ | 3+ | 0 | 0 | 0 | 0 |
| 24 | 1.0 | 3 | 3 | 3+ | 3+ | 0 | 0 | 0 | 0 |
| 24 | 0.5 | 3 | 3 | 3+ | 3+ | 0 | 0 | 0 | 0 |

TABLE 6b

| Compound No | Application Rate kg/ha | Test Plant | | | | | | | |
|---|---|---|---|---|---|---|---|---|---|
| | | Wh | Ot | Rg | Jm | P | Ip | Ms | Sf |
| 32 | 5.0 | 4 | 0 | 5 | 5 | 0 | 0 | 0 | 0 |
| 32 | 1.0 | 3 | 0 | 1 | 4 | 0 | 0 | 0 | 0 |
| 34 | 5.0 | 5 | 5 | 5 | 5 | 0 | 5 | 3 | 0 |
| 34 | 1.0 | 5 | 5 | 5 | 5 | 0 | 0 | 0 | 0 |
| 34 | 0.5 | 5 | 4 | 5 | 5 | 0 | 0 | 0 | 0 |
| 34 | 0.25 | 4 | 4 | 5 | 5 | 0 | 0 | 0 | 0 |
| 35 | 5.0 | 4 | 5 | 5 | 5 | 0 | 0 | 0 | 0 |
| 35 | 1.0 | 0 | 1 | 3 | 4 | 0 | 0 | 0 | 0 |
| 37 | 5.0 | 5 | 5 | 5 | 5 | 0 | 0 | 0 | 0 |
| 37 | 1.0 | 5 | 2 | 3 | 5 | 0 | 0 | 0 | 0 |
| 39 | 5.0 | 3 | 0 | 4 | 3 | 0 | 0 | 0 | 0 |
| 39 | 1.0 | 4 | 0 | 4 | 5 | 0 | 0 | 0 | 0 |
| 40 | 0.5 | 2 | 0 | 4 | 5 | 0 | 0 | 0 | 0 |
| 41 | 5.0 | 0 | 5 | 5 | 4 | 0 | 0 | 0 | 0 |
| 41 | 1.0 | 1 | 2 | 4 | 0 | 0 | 0 | 0 | 0 |
| 42 | 5.0 | 0 | 4 | 5 | 4 | 0 | 0 | 0 | 0 |
| 42 | 1.0 | 0 | 0 | 3 | 0 | 0 | 0 | 0 | 0 |
| 45 | 5.0 | 5 | 5 | 5 | 5 | 0 | 0 | 0 | 0 |
| 45 | 1.0 | 4 | 5 | 5 | 5 | 0 | 0 | 0 | 0 |
| 45 | 0.5 | 1 | 4 | 5 | 5 | 0 | 0 | 0 | 0 |
| 45 | 0.25 | 0 | 0 | 5 | 5 | 0 | 0 | 0 | 0 |

TABLE 6b-continued

| Compound No | Application Rate kg/ha | Test Plant | | | | | | | |
|---|---|---|---|---|---|---|---|---|---|
| | | Wh | Ot | Rg | Jm | P | Ip | Ms | Sf |
| 61 | 5.0 | 4 | 4 | 5 | 5 | 0 | 0 | 0 | 0 |
| 61 | 1.0 | 2 | 2 | 3 | 4 | 0 | 0 | 0 | 0 |
| 78 | 5.0 | 2 | 0 | 5 | 5 | 0 | 0 | 0 | 0 |
| 78 | 1.0 | 0 | 0 | 3 | 0 | 0 | 0 | 0 | 0 |

EXAMPLE 43

The compounds were formulated for test by mixing an appropriate amount with 5 ml of an emulsion prepared by diluting 160 ml of a solution containing 21.8 g per liter of "Span" 80 and 78.2 g per liter of "Tween" 20 in methylcyclohexanone to 500 ml with water. "Span" 80 is a Trade Mark for a surface-active agent comprising sorbitan monolaurate. "Tween" 20 is a Trade Mark for a surface-active agent comprising a condensate of sorbitan monolaurate with 20 molar proportions of ethylene oxide. Each 5 ml emulsion containing a test compound was then diluted to 40 ml with water and sprayed on to young pot plants (post-emergence test) of the species named in Table 7 below. Damage to test plants was assessed after 14 days on a scale of 0 to 5 where 0 is 0 to 20% damage and 5 is complete kill. In a test for pre-emergence herbicidal activity, seeds of the test plants were sown in a shallow slit formed in the surface of soil in fibre trays. The surface was then levelled and sprayed, and fresh soil then spread thinly over the sprayed surface. Assessment of herbicidal damage was carried out after 21 days using the same scale of 0 to 5 as the post-emergence test. In both cases the degree of herbicidal damage was assessed by comparison with untreated control plants. The results are given in Table 7 below. A dash (—) means that no experiment was carried out.

The names of the test plants were as follows:

| | |
|---|---|
| Sb | Sugar beet |
| Rp | Rape |
| Ct | Cotton |
| Sy | Soy bean |
| Mz | Maize |
| Ww | Winter wheat |
| Rc | Rice |
| Sn | Senecio vulgaris |
| Ip | Ipomea purpurea |
| Am | Amaranthus retroflexus |
| Pi | Polygonum aviculare |
| Ca | Chenopodium album |
| Ga | Galium aparine |
| Xa | Xanthium pensylvanicum |
| Ab | Abutilon theophrasti |
| Cv | Convolvulus arvensis |
| Co | Cassia obtusifolia |
| Av | Avena fatua |
| Dg | Digitaria sanguinalis |
| Al | Alopecurus myosuroides |
| St | Setaria viridis |
| Ec | Echinochloa crus-galli |
| Sh | Sorghum halepense |
| Ag | Agropyron repens |
| Cn | Cyperus rotundas |

TABLE 7
PART A

| Compound No | APPLICATION Method | Rate (kg/ha) | Sb | Rp | Ct | Sy | Mz | Ww | Rc | Sn | Ip | Am | Pi | Ca |
|---|---|---|---|---|---|---|---|---|---|---|---|---|---|---|
| 23 | PRE | 0.5 | 0 | 0 | 1 | 0 | 0 | — | — | 0 | 0 | 0 | 0 | 1 |
| 23 | POST | 0.5 | 0 | 1 | 1 | 0 | 4 | 1 | 0 | 1 | 0 | — | 0 | 0 |
| 24 | PRE | 2.0 | 0 | 2 | 0 | 0 | 0 | 4 | 1 | — | 0 | 0 | 0 | 0 |
| 24 | PRE | 0.5 | 0 | 0 | — | 0 | 0 | 1 | 0 | 1 | 0 | 0 | 0 | 0 |
| 24 | POST | 2.0 | 0 | — | 0 | 0 | 5 | 3 | — | 1 | 1 | — | 1 | — |
| 24 | POST | 0.5 | 0 | — | 0 | 1 | 5 | 4 | 0 | 0 | 0 | — | 0 | — |
| 28 | PRE | 2.0 | 0 | 0 | 0 | 1 | 2 | 4 | 4 | 0 | 0 | 0 | 0 | 0 |
| 28 | PRE | 0.5 | 0 | 0 | 0 | 0 | 0 | 2 | 2 | 0 | 0 | 0 | 0 | 0 |
| 28 | POST | 2.0 | 0 | — | 0 | 0 | 3 | 2 | — | 0 | 0 | — | 0 | 0 |
| 28 | POST | 0.5 | 0 | 0 | 0 | 0 | 1 | 1 | — | 0 | 1 | — | 0 | — |
| 29 | PRE | 2.0 | 0 | 0 | 0 | 0 | 2 | 2 | 0 | 0 | 0 | 0 | 0 | 0 |
| 29 | PRE | 0.5 | 0 | 0 | — | 0 | 0 | 0 | 1 | 0 | 0 | 0 | 0 | 0 |
| 29 | POST | 2.0 | 0 | 0 | 0 | 1 | 5 | 4 | — | 0 | 0 | — | 0 | — |
| 29 | POST | 0.5 | 0 | — | 0 | 0 | 5 | 3 | — | 0 | 0 | — | 0 | — |
| 32 | PRE | 2.0 | — | — | — | — | 1 | 2 | 2 | — | — | — | — | — |
| 32 | PRE | 0.5 | — | — | — | — | 0 | 0 | 0 | — | — | — | — | — |
| 32 | POST | 2.0 | — | — | — | — | 2 | 4 | 4 | — | — | — | — | — |
| 32 | POST | 0.5 | — | — | — | — | 1 | 4 | 3 | — | — | — | — | — |
| 34 | PRE | 2.0 | — | — | — | — | 3 | 5 | 5 | — | — | — | — | — |
| 34 | PRE | 0.5 | — | — | — | — | 0 | 4 | 4 | — | — | — | — | — |
| 34 | POST | 2.0 | — | — | — | — | 4 | 4 | 5 | — | — | — | — | — |
| 34 | POST | 0.5 | — | — | — | — | 3 | 4 | 3 | — | — | — | — | — |

TABLE 7
PART B

| Compound No | APPLICATION Method | Rate (kg/ha) | Ga | Xa | Ab | Cv | Av | Dg | Al | St | Ec | Sh | Ag | Cn |
|---|---|---|---|---|---|---|---|---|---|---|---|---|---|---|
| 23 | PRE | 0.5 | 0 | — | 0 | 1 | — | 2 | — | 0 | — | — | 0 | 0 |
| 23 | POST | 0.5 | 0 | — | 0 | 0 | 2 | 5 | 2 | 4 | 0 | 3 | 0 | 0 |
| 24 | PRE | 2.0 | 0 | 0 | 0 | 0 | 3 | 4 | 5 | 3 | 2 | 2 | 4 | 0 |
| 24 | PRE | 0.5 | 0 | 0 | 0 | 0 | 1 | 2 | 3 | 0 | 0 | 0 | 2 | 0 |
| 24 | POST | 2.0 | 0 | 0 | 0 | 3 | 4 | 5 | 5 | 5 | 5 | 4 | 4 | 0 |
| 24 | POST | 0.5 | 0 | — | 0 | 0 | 3 | 5 | 5 | 4 | 5 | 4 | 2 | 0 |
| 28 | PRE | 2.0 | 0 | 0 | 0 | 1 | 2 | 4 | 5 | 3 | 5 | 4 | 4 | 0 |
| 28 | PRE | 0.5 | 0 | 0 | — | 0 | 0 | 1 | 4 | 0 | 4 | 2 | 3 | 0 |
| 28 | POST | 2.0 | 0 | 0 | 0 | 1 | 0 | 4 | 4 | 4 | 4 | 5 | 1 | 0 |
| 28 | POST | 0.5 | 0 | 0 | 0 | 0 | 0 | 4 | 4 | 2 | 4 | 4 | 1 | 0 |
| 29 | PRE | 2.0 | 0 | 0 | — | 0 | 0 | 1 | 4 | 1 | 3 | 2 | 4 | 0 |
| 29 | PRE | 0.5 | 0 | 0 | — | 0 | 0 | 0 | 3 | 1 | 0 | 0 | 1 | 0 |
| 29 | POST | 2.0 | 0 | 0 | 2 | 2 | 0 | 5 | 4 | 4 | 5 | 4 | 1 | 0 |
| 29 | POST | 0.5 | 0 | 0 | 0 | 0 | 0 | 3 | 4 | 3 | 4 | 1 | 0 | 0 |
| 32 | PRE | 2.0 | — | — | — | — | 1 | 4 | 3 | 2 | 1 | 0 | 4 | 0 |
| 32 | PRE | 0.5 | — | — | — | — | 0 | 3 | 2 | 1 | 0 | 0 | 0 | 0 |
| 32 | POST | 2.0 | — | — | — | — | 2 | 5 | 4 | 4 | 5 | 5 | 4 | 0 |
| 32 | POST | 0.5 | — | — | — | — | 1 | 4 | 3 | 4 | 4 | 4 | 2 | 0 |
| 34 | PRE | 2.0 | — | — | — | — | 3 | 5 | 5 | 1 | 3 | 4 | 5 | 0 |
| 34 | PRE | 0.5 | — | — | — | — | 1 | 3 | 5 | 0 | 0 | 3 | 4 | 0 |
| 34 | POST | 2.0 | — | — | — | — | 4 | 4 | 4 | 5 | 5 | 5 | 5 | 3 |
| 34 | POST | 0.5 | — | — | — | — | — | 4 | 4 | 4 | 5 | 5 | 4 | 2 |

We claim:

1. A compound of the formula

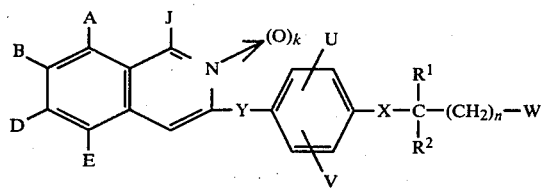

wherein:
A, D, E, U, V and R² are hydrogen;
B is halogen;
J is halogen;
R¹ is methyl;
W is the group

wherein G is selected from the group consisting of hydroxy, $C_1$ to $C_{10}$ alkoxy, $C_2$ to $C_{10}$ alkenyloxy, $C_2$ to $C_{10}$ alkynyloxy, and the group OM wherein M is an alkali metal or alkaline earth metal ion;
X is oxygen;
Y is selected from oxygen and the group $NR^6$ wherein $R^6$ is methyl; and
k and n are both 0.

2. A compound according to claim 1 wherein:
A, D, E, U, V and R² are hydrogen;
B and J are halogens;
R¹ is methyl;
W is the group

wherein G is chosen from the group consisting of hydroxy, $C_1$ to $C_6$ alkoxy and the group OM wherein M is an alkali metal ion;
X is oxygen;
Y is chosen from oxygen and the group $NR^6$ wherein $R^6$ is methyl; and
k and n are both 0.

3. A compound according to claim 2 wherein:
A, D, E, U, V and $R^2$ are hydrogen;
B and J are chosen from fluorine, chlorine and bromine;
$R^1$ is methyl;
W is the group

wherein G is chosen from the group consisting of hydroxy, $C_1$ to $C_6$ alkoxy and the group OM wherein M is sodium or potassium;
X and Y are both oxygen; and
k and n are both 0.

4. A compound according to claim 2 wherein:
A, D, E, U, V and $R^2$ are hydrogen;
B is chosen from fluorine and chlorine;
J is chlorine;
$R^1$ is methyl;
W is the group

wherein G is chosen from the group consisting of hydroxy, $C_1$ to $C_6$ alkoxy and the group OM wherein M is sodium or potassium;
X is oxygen;
Y is the group $NR^6$ wherein $R^6$ is methyl; and
k and n are both 0.

5. A herbicidal composition comprising as active ingredient a compound as defined according to claim 1 and a carrier therefor.

6. A process for severely damaging or killing unwanted plants which process comprises applying to said plants, or to the growth medium of said plants, an effective amount of a compound as defined according to claim 1.

7. A process for selectively controlling the growth of monocotyledonous weeds in dicotyledonous crops which process comprises applying to said crop, or to the growth medium of said crop, a compound as defined according to claim 1 in an amount sufficient to substantially damage the crop.

8. A process according to claim 6 wherein the compound is applied at a rate in the range from 0.005 to 20 kilograms per hectare.

* * * * *